(12) United States Patent
Ahrens et al.

(10) Patent No.: US 10,059,950 B2
(45) Date of Patent: Aug. 28, 2018

(54) COMPOSITIONS COMPRISING AN INTERNALIZING NUCLEIC ACID MOLECULE, AND THEIR METHODS OF USE

(71) Applicant: B3 BIO, INC., Research Triangle Park, NC (US)

(72) Inventors: Doug Ahrens, Apex, NC (US); Ashley Barry, Morrisville, NC (US); Michael Greenberg

(73) Assignee: Upstream Technologies, Inc., Durham, NC (US)

( * ) Notice: Subject to any disclaimer, the term of this patent is extended or adjusted under 35 U.S.C. 154(b) by 294 days.

(21) Appl. No.: 14/394,797

(22) PCT Filed: Apr. 17, 2013

(86) PCT No.: PCT/US2013/036896
§ 371 (c)(1),
(2) Date: Oct. 16, 2014

(87) PCT Pub. No.: WO2013/158717
PCT Pub. Date: Oct. 24, 2013

(65) Prior Publication Data
US 2017/0240895 A1    Aug. 24, 2017

Related U.S. Application Data

(60) Provisional application No. 61/625,363, filed on Apr. 17, 2012.

(51) Int. Cl.
*C12N 15/115*    (2010.01)

(52) U.S. Cl.
CPC ........ *C12N 15/115* (2013.01); *C12N 2310/16* (2013.01); *C12N 2310/351* (2013.01); *C12N 2310/531* (2013.01); *C12N 2320/32* (2013.01)

(58) Field of Classification Search
None
See application file for complete search history.

(56) References Cited

U.S. PATENT DOCUMENTS

| | | |
|---|---|---|
| 2008/0261277 A1 | 10/2008 | Guo et al. |
| 2010/0029003 A1 | 2/2010 | Bartel et al. |
| 2011/0244025 A1* | 10/2011 | Uhlmann ............... C07H 21/00 424/450 |

FOREIGN PATENT DOCUMENTS

EP    2839002 B1    10/2017

OTHER PUBLICATIONS

Villa et al.; Molecular Dynamics Simulations of The Structure, Dynamics, and Thermostability of the RNA Hairpins uCACCg and cUUCGg; J. Phys. Chem. B. 2008, 112:134-142.
Meyer et al.; Cell-specific Aptamers as Emerging Therapeutics; J. Nucleic Acids; 2011(4968):904750.
Orva et al.; Delivering cargoes into cancer cells using DNA aptamers targeting internalized surface portals; Biochimica et Biophysica Acta 1798 (2010) 2190-2200.
Shigdar et al.; RNA aptamer against a cancer stem cell marker epithelial cell adhesion molecule; Cancer Sci; 2011, 102(5):991-998.
Zhou and Rossi; Aptamer-targeted cell-specific RNA interference; Silence, 2010, 1-4.

* cited by examiner

*Primary Examiner* — Robert M Kelly
(74) *Attorney, Agent, or Firm* — M. Bud Nelson

(57) ABSTRACT

Provided are internalizing nucleic acid molecules ("iNA") that can bind and internalize into target cells containing a cell surface molecule to which the iNA can bind; an iNA further modified to include at least one chemical modification, wherein the at least one modification is selected from the group consisting of a chemical substitution in the nucleic acid sequence of the iNA, incorporation of a modified nucleotide into the iNA, conjugation to a linker, and conjugation to at least one effector moiety comprising one or more of a drug or a detectable moiety or a combination thereof; and methods of using modified iNA to deliver at least one effector moiety into the target cells.

12 Claims, 7 Drawing Sheets

Specification includes a Sequence Listing.

COMPOSITIONS COMPRISING AN INTERNALIZING NUCLEIC ACID MOLECULE, AND THEIR METHODS OF USE

This invention was made with government support under Grant No. 1R43CA141725-01A1, awarded by the National Institutes of Health. The government has certain rights in the invention.

FIELD OF THE INVENTION

The present invention relates generally to the field of internalizing nucleic acid molecules ("iNAs"), and more particularly to a nucleic acid molecule that is capable of binding to and internalizing into cancer cells of different tissue origin. The iNAs are also useful for delivering therapeutics or diagnostics into cancer cells, and/or cells implicated in other diseases or disorders, which express a molecule on their cell surface recognized by the iNAs of the invention.

BACKGROUND OF THE INVENTION

Cancer remains a leading cause of mortality and morbidity and, therefore, desired are anticancer treatments that are more efficacious, and have fewer side effects, than existing therapies. Currently, there is an unmet need for enhanced targeting of therapeutic agents in the treatment of cancer. While potent cytotoxic agents have been (and continued to be) developed as anticancer agents, without targeted delivery to the tumor environment, the cytotoxic agents are distributed throughout the body (in systemic administration) or tissue (in a localized administration). As a result, there is a need for higher dosing levels to achieve a therapeutically effective amount of cytotoxic agent at the site of the tumor, and exposure of non-targeted cells to the cytotoxic agent which often results in undesired side effects or overt dose limiting toxicities.

Prostate cancer is the most common form of cancer and the second leading cause of death among men in the United States. Treatment of prostate cancer is complicated by the fact that the disease progresses through various stages of malignancy, such as androgen-dependence, androgen independence, and metastasis. In this regard, prostate cancer cells can vary in their expression of cell surface molecules as they progress through the various stages of malignancy. Targeted delivery directed to PSMA-expressing ("PSMA(+)") prostate cancer cells has been proposed using an aptamer that binds to PSMA (prostate-specific membrane antigen). While a number of studies have shown that expression of PSMA is a sensitive and specific marker for prostate adenocarcinoma, approximately one third of prostate adenocarcinoma lack detectable cell surface expression of PSMA ("PSMA (−)").

SUMMARY OF THE INVENTION

Provided as an aspect of the invention is a composition comprising a nucleic acid molecule that binds to cancer cells (such as cells from cancers originating from one or more organs or tissues; or cell lines established therefrom), and mediates internalization of the nucleic acid molecule into a cell expressing a cell surface molecule for which the nucleic acid molecule has binding specificity (hence, the nucleic acid molecule is referred to as an "internalizing nucleic acid molecule", abbreviated as "iNA"). The composition may further comprise a conjugate which comprises the iNA linked to a molecule that is useful in treating and/or detecting cells expressing a cell surface molecule for which the nucleic acid molecule has binding specificity.

Provided is an iNA that specifically bind to a cell surface molecule differentially expressed by cancer cells, as compared to healthy tissue tested to date, for which the nucleic acid molecule has binding specificity. In one embodiment, the iNA comprises a nucleic acid sequence comprising from about 20 nucleotides to about 70 nucleotides. In another embodiment, the iNA further contains a motif of one or more of UUUCGG, UUUCGGGC, (UUUCGG)$N_m$(UUUCGG)$_n$ (SEQ ID NO:22), wherein n is a number from one to four, and between repeats of UUUCGG is one or more nucleotides N, wherein N can be any one or more of A, U, C, or G, and m is a number from 0 to 4 to signify the number of N bases; and wherein the motif is present in at least one loop portion of a stem-loop structure. In some embodiments, an iNA of the invention has substantially the same ability to bind cancer cells as that of an iNA comprising a motif of contiguous nucleotides represented by SEQ ID NO:22. Surprisingly, as shown herein, these iNAs have been found to bind and internalize into human cancer cells representative of various types of malignancy (e.g., prostate cancer, breast cancer, chronic myelogenous leukemia, B cell lymphoma, glioblastoma multiforme, epidermoid carcinoma), as well as to human cancer cells from various stages of malignancy, but not detectably to human cells of normal (non-malignant) tissue tested. The iNA may be used alone, or in modified form (e.g., further modified to comprise at least one chemical modification), in a pharmaceutical composition which further comprises a pharmaceutically acceptable carrier, or in the manufacture of a medicament for treating a disease. The iNA may be further modified to include at least one chemical modification, wherein the at least one modification is selected from the group consisting of a chemical substitution in the nucleic acid sequence (e.g., a chemical substitution at a sugar position of one or more nucleotides, a chemical substitution at a phosphate position of one or more nucleotides, and a chemical substitution at a base position of one or more nucleotides), incorporation of a modified nucleotide, conjugation to a linker, and conjugation to an effector moiety comprising a drug, a detectable moiety (e.g., a molecule detectable by any one of fluorescence, luminescence, chromogenicity, radioactivity, enzyme activity) or a combination thereof. The iNA or modified iNA may be provided in isolated form (e.g., substantially free from reactants, such as chemicals, enzymes, and reagents, used in the synthesis of the iNA or modified iNA). Also provided is a method of specifically delivering an effector moiety to cancer cells, comprising the steps of contacting the cancer cells with an iNA which is coupled to an effector moiety (with or without use of a linker), wherein the iNA specifically binds to an extracellular portion or epitope of a cell surface molecule for which the nucleic acid molecule has binding specificity, wherein the effector moiety is delivered to the cancer cells. In one aspect of the invention, delivery to the cells comprises internalization of one or more of (a) the iNA coupled to the effector moiety, or (b) the effector moiety itself, into the cancer cells contacted by the iNA coupled to an effector moiety.

An embodiment of the invention provides a tumor-specific drug conjugate comprised of (a) an internalizing nucleic acid molecule comprised of RNA that binds to a cell surface molecule for which the nucleic acid molecule has binding specificity on tumor cells, wherein the internalizing nucleic acid molecule recognizes a cell surface molecule other than prostate-specific membrane antigen, wherein the internalizing nucleic acid molecule is capable of binding to and internalizing into more than one type of cancer ("type" referring to anatomical origin or tissue type origin, e.g., more than one of: breast cancer, prostate cancer, glioblastoma, leukemia, lymphoma, colorectal carcinoma, ovarian cancer, lung cancer, stomach cancer, bladder cancer, liver cancer, and colon cancer), in providing a targeting agent that has both the specificity for targeting tumors and the ability to internalize into tumor cells; (b) a linker which is used to couple the internalizing nucleic acid molecule to a cytotoxic drug; and (c) a cytotoxin, such as a drug that is cytotoxic.

In another aspect of the invention, provided are methods for delivering the iNA, or pharmaceutical composition comprising the iNA, to target cells which express a cell surface molecule for which the nucleic acid molecule has binding specificity, in which cells a modification of a biological process is desired, such as in the treatment of diseases or other medical conditions such as cancer, pre-cancerous conditions (e.g., chronic inflammation as a progenitor to the development of tumor, metaplasia, hyperplasia, dysplasia, and polyps), and cell proliferative and/or differentiative disorders. The method of treating a disease with a pharmaceutical composition according to the invention may further comprise use in combination with one or more other therapeutics, such that the combination therapy acts to enhance or amplify a therapeutic effect, as compared to use without combination therapy. Thus, provided is a method of delivering a therapeutic agent to target cells which express a cell surface molecule for which the nucleic acid molecule has binding specificity, the method comprising contacting the target cells with an iNA further modified to include at least one chemical modification, wherein the at least one modification is selected from the group consisting of a chemical substitution in the nucleic acid sequence, incorporation of a modified nucleotide, conjugation to a linker, and conjugation to an effector moiety comprising a drug, a detectable moiety, and a combination thereof. With the binding specificity of the iNA for the target cells, the therapeutic agent is delivered to primarily target cells, and minimally to cells other than target cells.

Also provided is a method of delivering at least one effector moiety into target cells, the method comprising: contacting the target cells with an iNA modified to include at least one effector moiety, wherein the at least one effector moiety comprises a drug, a detectable moiety, or a combination thereof; wherein the iNA comprises at least one stem-loop structure as predicted by an RNA folding algorithm, and further comprises, in at least one loop portion of a stem-loop structure, a nucleic acid sequence that comprises a nucleotide sequence containing at least one conserved motif (e.g., UUUCGG; UUUCGGGC; (UUUCGG)N$_m$ (UUUCGG)$_n$ (SEQ ID NO:22), or a combination thereof), wherein n is a number from one to four, and between repeats UUUCGG is one or more nucleotides N, wherein N can be any one or more of A, U, C, or G, and m is a number from 0 to 4 to signify the number of N bases; or a combination thereof); and wherein the modified iNA is internalized into the target cells in delivering the at least one effector moiety into the target cells.

Also provided is a method of treating, preventing, and/or ameliorating a disease or condition associated with expression of a cell surface molecule for which the nucleic acid molecule has binding specificity, the method comprising administering a pharmaceutical composition of the invention to an individual having disease associated with expression of the cell surface molecule for which the nucleic acid molecule has binding specificity, wherein the composition is administered in an amount effective to treat, prevent, and/or ameliorate the disease or condition.

Further provided is an iNA that binds to cells expressing a cell surface molecule for which the nucleic acid molecule has binding specificity, and mediates internalization into such cells; wherein the iNA may be used for one or more of in vitro diagnostics or in vivo diagnostics. For example, for use in in vivo diagnostics, the iNA may be chemically modified by conjugation to a metal chelating agent to enable labeling with radioisotopes for in vivo detection using standard imaging techniques for radioisotopes. A detection method according to the invention comprises contacting cells with a composition, comprising an iNA of the invention chemically modified to be linked or coupled to a detectable moiety, and detecting the presence or absence of detectable moiety associated with the cells; wherein cells, that are detected as containing the detectable moiety, comprise cells expressing a cell surface molecule for which the iNA has binding specificity and with which mediates internalization. In some embodiments, the diagnostic method is for use in vivo, and in other embodiments, the diagnostic method is for use in vitro. With the binding specificity of the iNA for cells expressing a cell surface molecule for which the iNA has binding specificity and with which mediates internalization, other cells (lacking expression of such cell surface molecule) will minimally or not be detected.

Other aspects, objects and features of the invention will be apparent from the following description.

BRIEF DESCRIPTION OF THE DRAWINGS

FIG. 1A and FIG. 1B are secondary structure schematics, as predicted and generated by RNA-folding algorithms, containing one or more conserved motifs, wherein FIG. 1A is a secondary structure schematic for a full length (including the 5' and 3' fixed regions) iNA having a variable region comprising a sequence comprising SEQ ID NO:19; and FIG. 1B is a secondary structure schematic for a full length iNA having a variable region comprising a sequence comprising SEQ ID NO:20.

FIG. 2A, FIG. 2B, FIG. 2C, and FIG. 2D are secondary structure schematics, as predicted and generated by RNA-folding algorithms, containing one or more conserved motifs, wherein FIG. 2A is a secondary structure schematic for an iNA comprising a nucleotide sequence comprising SEQ ID NO:25; FIG. 2B is a secondary structure for an iNA comprising a nucleotide sequence comprising SEQ ID NO:26; FIG. 2C is a secondary structure schematic for an iNA comprising a nucleotide sequence comprising SEQ ID NO:27; and FIG. 2D is a secondary structure schematic for an iNA comprising a nucleotide sequence comprising SEQ ID NO:28.

DETAILED DESCRIPTION OF THE INVENTION

Figure 1A:
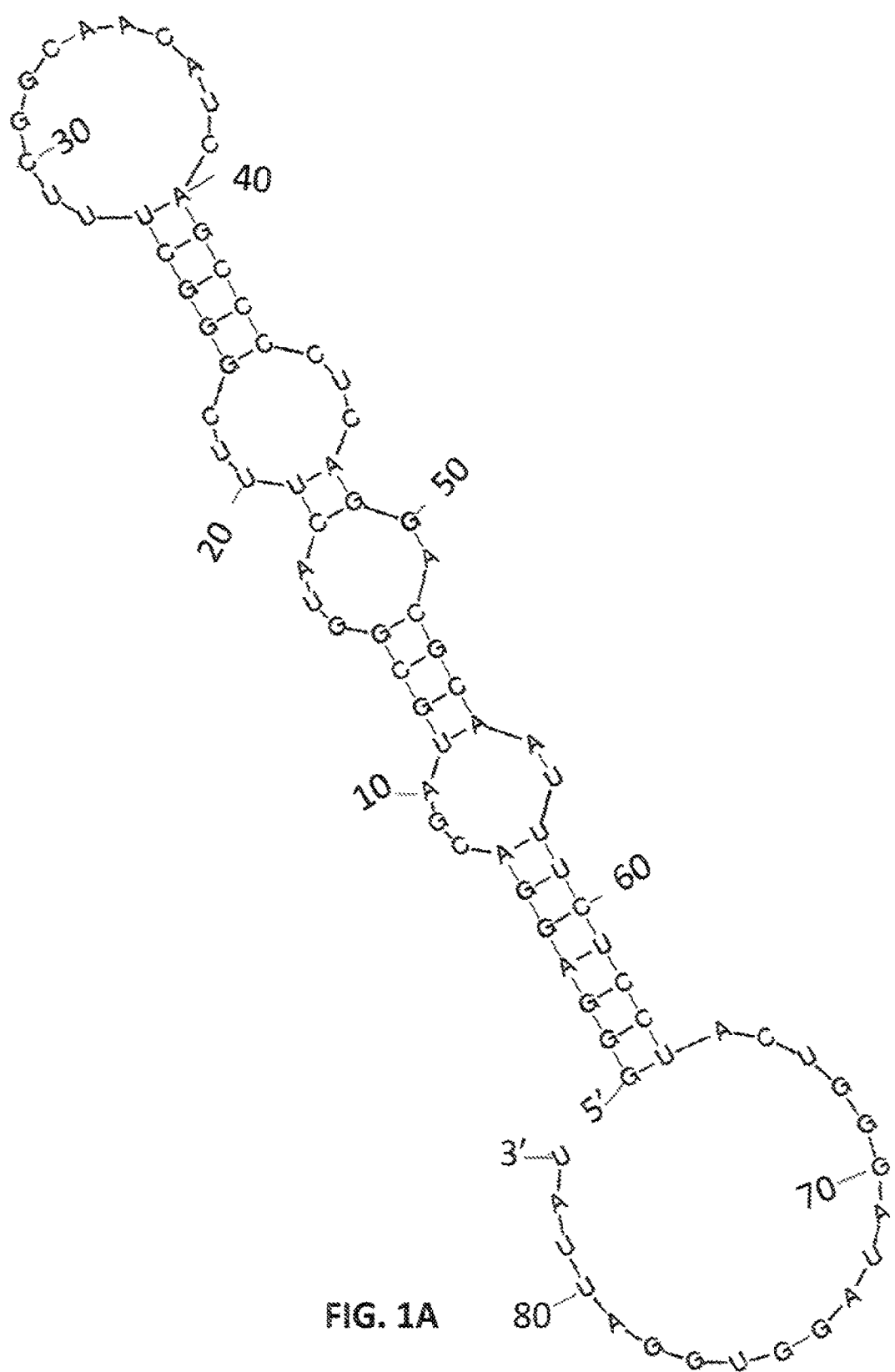

The invention relates to internalizing nucleic acid molecules ("iNA" that specifically bind to cells expressing a cell surface molecule for which the nucleic acid molecule has binding specificity, and that mediates internalization into the cells. Thus, the iNA (and any modification thereto) may be internalized into cells expressing a cell surface molecule for which the nucleic acid molecule has binding specificity, and more preferably into human cancer cells. The iNA may be further modified to include at least one chemical modification, wherein the at least one modification is selected from the group consisting of a chemical substitution in the nucleic acid sequence, incorporation of a modified nucleotide, conjugation to a linker, and conjugation to an effector moiety comprising a drug, a detectable moiety, or a combination thereof.

Definitions—While the following terms are believed to be well understood by one of ordinary skill in the art of biotechnology, the following definitions are set forth to facilitate explanation of the invention.

The term "amino acid", as used herein, refers to naturally occurring amino acids, unnatural amino acids, as well as amino acid analogs. Naturally occurring amino acids are those encoded by the genetic code, whereas unnatural amino acids are represented by D-amino acids (the "D" stereochemical form of a naturally occurring amino acid). Amino acid analogs refer to those amino acids that basically have the same chemical structure as a naturally occurring amino acid, except have a modified R group or modified peptide backbone. For example, as illustrated herein for a cleavable linker comprising at least two amino acids, one of such amino acids may be citrulline (a precursor to arginine).

The terms "cell" or "cells", as used herein, refers to one or more cells or cell types of mammalian origin, and more desirably of human origin. "Target cells" refers to cells expressing, on their cell surface, one or more molecules for which the nucleic acid molecule has binding specificity, wherein upon the cells binding with the iNA (via the cell surface molecule), mediated is internalization of the iNA into the cells.

The term "cytotoxic", as used herein in connection with a cytotoxin, means killing, or arresting the growth of, cells.

The terms "first" and "second" are used herein for purposes of distinguishing between two molecules, or between two moieties, or between two different positions on a molecule, as will be clearer from the description.

The terms "internalizing nucleic acid molecule" or "iNA", are used interchangeably herein, refer to a nucleic acid molecule: (a) of from about 20 nucleotides to about 80 nucleotides, and often is from about 30 nucleotides to 65 nucleotides in length; (b) binds to a molecule found on the surface of a cell; and (c) which, following binding to the cell surface molecule, is internalized or transported into a cell. An iNA may be comprised of DNA, or RNA, or a combination thereof. An iNA may comprise a chemical modification comprising incorporation of one or more modified nucleic acid bases (e.g., modified nucleotides), for example, to improve pharmacokinetics and/or stability (e.g., against nucleases) when administered in vivo. For example, modified purines are know to include, but are not limited to, 2'-O-methyl nucleotides; and modified pyrimidines are known to include, but are not limited to, 2'-deoxy-2'-fluoro nucleotides or 2'-deoxy-2'-fluoroarabino nucleotides. Thus, chemical modifications of nucleotides for iNA may include, without limitation, phosphorothioate internucleotide linkages, 2'-deoxyribonucleotides, 2'-O-methyl ribonucleotides, 2'-deoxy-2'-fluoro ribonucleotides, 4'-thio ribonucleotides, 2'-O-trifluoromethyl nucleotides, 2'-O-ethyl-trifluoromethoxy nucleotides, 2'-O-difluoromethoxy-ethoxy nucleotides, L-nucleotides, and 5-C-methyl nucleotides. With respect to the present invention, the iNA binds to a cell surface molecule for which the nucleic acid molecule has binding specificity, with an affinity represented by a $K_D$ (dissociation constant) of no more than about 100 nM, and preferably a $K_D$ no greater than 75 nM, or a $K_D$ no greater than 50 nM, or a $K_D$ no greater than 25 nM, or a $K_D$ no greater than 10 nM, or a $K_D$ less than 10 nM. The term "conserved motif", used herein for purposes of the specification and claims, refers to a nucleotide sequence: (a) comprising from about 5 to about 20 contiguous nucleotides (see e.g., UUUCGG; UUUCGGGC; (UUUCGG)$N_m$(UUUCGG)$_n$ (SEQ ID NO:22), or a combination thereof); (b) which consists of conserved sequence elements (for example, as determined by sharing of that motif in the sequences of more than one iNA having binding capability for the same cell surface molecule, and that mediates internalization into the cells); and (c) is observed in a characteristic pattern of occurrence in a preferred position or region of the binding portion of the iNA nucleotide sequence, such as in at least one loop portion of a stem-loop structure in an iNA having at least one stem-loop structure as predicted by an RNA folding algorithm. Having at least one conserved motif may play a role in formation of a structure necessary for binding to a cell surface molecule for which the nucleic acid molecule has binding specificity, and through which mediates internalization into the cells. In this regard, with the aid of commercially available motif searching software, and RNA folding software in analyzing multiple clones selected for by one or more methods for selection for binding affinity to cancer cells, a conserved motif was identified, along with their characteristic pattern of occurrence in the iNA sequence (see, e.g., Table 4). Thus, in one embodiment, an iNA according to the present invention comprises one or more of: (a) a nucleic acid sequence that contains a nucleotide sequence comprising at least one conserved motif (e.g., UUUCGG; or UUUCGGGC; or a repeat of (UUUCGG)$N_m$(UUUCGG)$_n$ (SEQ ID NO:22), wherein n is a number from one to four, and between repeats UUUCGG is one or more nucleotides N, wherein N can be any one or more of A, U, C, or G, and m is a number from 0 to 4 to signify the number of N bases; or a combination thereof); and wherein the nucleic acid binds to, and is internalized by, cells expressing a cell surface molecule to which the nucleic acid molecule has binding specificity; or (b) an iNA of from 20 to about 60 contiguous nucleotides that has substantially the same ability to bind to, and is internalized by the cell expressing the cell surface molecule to which the iNA binds, as an iNA with a conserved motif according to the invention. In another embodiment, an iNA may have at least 70% identity, 75% identity, 80% identity, 85% identity, 90% identity, 95% identity, and up to 99% identity with the nucleic acid sequence of an iNA comprising the nucleotide sequences selected from one or more of SEQ ID NOs:25 and 38, or with an iNA's variable portion wherein the variable portion comprises a nucleotide sequence selected from one or more of SEQ ID NOs:19 and 20; provided (a) a conserved motif, appearing in one or more loops of the stem-loop structure of the iNA, is UUUCGG, or UUUCGGGC, or (UUUCGG)$N_m$(UUUCGG)$_n$ (SEQ ID NO:22); and (b) maintained is a at least one stem-loop structure as predicted by an RNA folding algorithm. The term "identity" in describing nucleic acid sequences, refers to a specified percentage of nucleotides that are the same, when compared and aligned for maximum correspondence, and as measured using either visual inspection or a sequence comparison algorithm known in the art such as GAP, BESTFIT, FASTA, BLASTN and TFASTA.

The term "detectable moiety", used herein, refers to a moiety having a detectable physical, biological, electrical, optical, enzymatic, photochemical, biochemical, immunochemical or chemical property.

The term "linker" is used herein to mean a chemical entity that connects two molecules together (e.g., connecting two different molecules together such as an iNA with an effector moiety such as a cytotoxin, or a detectable moiety). The linker may, optionally, further comprise a self-immolative spacer. As illustrated in some embodiments herein, in using an iNA to deliver an effector moiety to target cells, preferably the linker is cleavable by a process in vivo (e.g., enzymatic, reductive, pH-mediated) at a site comprising one or more of: near the target cells (e.g., enzymes which are encountered extracellularly in reference to the target cells, such as those produced in the tumor environment when the target cells are cancer cells) or inside the target cells (e.g., pH or enzymes encountered intracellularly such as in lysosomal/endosomal processes). As will be described herein in more detail, cleavable moieties in a linker are known to include, but are not limited to, peptide bonds, nucleotide bonds, disulfide linkages, hydrazone linkages, and ester linkages. The terms "preferential" and "preferentially" are used interchangeably herein, in conjunction with cleavage of a cleavable moiety of a cleavable linker, to mean that (a) substantially all or a majority of the cleavable moiety of the cleavable linker is cleaved in one or more of (i) the microenvironment of the target cells, and (ii) the target cells (i.e., cleaved intracellularly); and (b) no more than 25%, and typically no more than about 15%, more typically no more than 10%, more preferably no more than about 5% or no more than about 1%, of the cleavable moiety of a cleavable linker (used as at least one chemical modification of an iNA) is cleaved in blood in the first hour, or 2 hours, or longer, following administration of the chemically modified iNA. The sensitivity of a cleavable moiety of a cleavable linker to cleavage in blood can be determined using in vitro cleavage activity assays known in the art, using blood or blood products such as plasma or serum, or isolated enzymes.

The term "pharmaceutically acceptable carrier" is used herein to mean any compound or composition or carrier medium useful in any one or more of administration, delivery, storage, stability of a composition or iNA described herein. These carriers are known in the art to include, but are not limited to, water, saline, suitable vehicle (e.g., liposome, microparticle, nanoparticle, emulsion, capsule), buffer, medical parenteral vehicle, excipient, aqueous solution, suspension, solvent, emulsions, detergent, chelating agent, solubilizing agent, diluent, salt, colorant, polymer, hydrogel, surfactant, emulsifier, adjuvant, filler, preservative, stabilizer, oil, and the like as broadly known in the pharmaceutical art.

The term "self-immolative spacer" is used herein to refer to a bifunctional chemical moiety that is capable of covalently coupling together a first chemical moiety with a second chemical moiety into a stable tripartite molecule. Upon cleavage of the bond to the first chemical moiety of the tripartite molecule, the self-immolative spacer is capable of spontaneously separating from the second chemical moiety.

The term "reactive group" is used herein to mean a chemical group which is capable of being reacted with another chemical group in forming a bond. For example, a reactive group of amino acid, for attaching a peptide linker to an effector moiety comprising a cytotoxin or detectable moiety, or to an iNA using attachment chemistry known in the art, may include but is not limited to an amine, carboxyl, sulfhydryl, or hydroxyl group. In another example, a reactive group of a nucleotide, in attaching an iNA to either a linker, or effector moiety using attachment chemistry known in the art, may include but is not limited to a reactive group on a base (e.g., an exocyclic amine) or hydroxyl group on a sugar moiety. For example, for coupling a reactive group of a first molecule to a second molecule in forming a composition according to the invention, wherein the first molecule has a free amine group that can be reacted with an amine-reactive group, such amine-reactive groups may include, without limitation, a succinimidyl ester group, a sulfosuccinimidyl ester group, a tetrafluorophenyl ester group, a carbonyl azide group, an isocyanate group, a sulfonyl chloride group or an aldehyde-containing group. In another example, for coupling a reactive group of a first molecule to a second molecule in forming a composition according to the invention, wherein the first molecule has a free thiol group (also called sulfhydryl) that can be reacted with a thiol-reactive group, such thiol-reactive groups may include, without limitation, a maleimide group, an iodoacetamide group, a phenylmercury group, a thiosulfate group or a methyl bromide group. For example, for coupling a reactive group of a first molecule to a second molecule in forming a composition according to the invention, wherein the first molecule has a free carboxyl group that can be reacted with a carboxyl-reactive group, such carboxyl-reactive groups may include, without limitation, a hydrazide group, a hydroxylamine group, a cadaverine group or an amine group. The amino acid or nucleotide or linker or detectable moiety may be further modified at one or more sites to allow for the attachment of a desired reactive group onto the molecule (a non-limiting example being modifying the 5' end of an iNA with a thiophosphate), or can be modified and attached using a cross-linker moiety, including, without limitation, a homobifunctional crosslinker (e.g., including, without limitation, bis(maleimido)hexane or BMH; or DSP or Lomant's Reagent, with cleavable disulfide bond in the linker), or a heterobifunctional crosslinker (including, without limitation, Succinimidyl-6-[(β-maleimido-propionamido)hexanoate], SMPH; or N-Succinimidyl 3-(2-pyridyldithio)-propionate, SPDP, with cleavable disulfide bond in the linker). Succinimidyl-4-(N-maleimidomethyl)cyclohexane-1-carboxylate (SMCC) is a non-cleavable and membrane permeable heterobifunctional crosslinker contain an amine-reactive N-hydroxysuccinimide (NHS ester) and a sulfhydryl-reactive maleimide group.

Presented herein is a more detailed description of the invention. Certain aspects of the invention are described in greater detail in the non-limiting Examples that follows.

iNA

According to a one aspect of the invention, provided is an iNA that specifically bind to a cell surface molecule, such as on certain human cells, as described in more detail herein. Surprisingly, as shown herein, iNAs of the invention have been found to bind and internalize into human cancer cells representative of various types of malignancy, as well as to human cancer cells from various stages of malignancy, but not detectably to human cells of normal (non-malignant) tissue tested. The iNA may be used alone, or in modified form. The iNA may be further modified to include at least one chemical modification, wherein the at least one modification is selected from the group consisting of a chemical substitution in the nucleic acid sequence, incorporation of a modified nucleotide, conjugation to a linker, and conjugation to an effector moiety comprising a drug, a detectable moiety, or a combination thereof. When an iNA of the invention is modified by conjugation to an effector moiety, with or without the use of a linker between the iNA and the effector moiety, the iNA is not modified with a liposome containing the effector moiety; and hence, avoided is a decrease in specificity of a liposome-containing conjugate for the intended target cells caused by the liposomes' interactions with cell surface molecules on cells other than target cells. In one aspect, a chemical modification comprising conjugation involves covalent bond formation, and not via non-covalent association, except as otherwise described herein (e.g., as to the latter, conjugation may alternatively be by base-pairing when a nucleic acid-based linker is coupled by base paring to an iNA via hybridization). iNAs that have binding affinity and specificity for, and which are capable of being internalized by, a target cell, and which iNA may, optionally, be further modified, are disclosed herein (see Tables 4 & 5, Example 1). In one embodiment, an iNA of the invention comprises an RNA molecule of from about 20 nucleotides to about 65 nucleotides, while maintaining the ability to bind and internalize into target cells, wherein the RNA molecule comprises at least one stem-loop structure in which at least one loop portion of the at least one stem-loop structure comprises a nucleic acid sequence that has a nucleotide sequence of one or more of UUUCGG, UUUCGGGC, (UUUCGG)$N_m$(UUUCGG)$_n$ (SEQ ID NO:22), wherein n is a number from one to four, and wherein between repeats of UUUCGG (see, e.g., SEQ IF NO:22) is one or more nucleotides N, wherein N can be any one or more of A, U, C, or G, and m is a number from 0 to 4 to signify the number of N bases.

As known to one skilled in the art, a stem-loop structure means a secondary or three-dimensional structure comprising at least one stem portion having a stem-like shape formed by two regions of the same nucleic acid molecule which complementary bind together (e.g., intramolecular base pairing); and at least one loop portion, typically extending from a stem portion. A loop portion is primarily a single-stranded region of the nucleic acid molecule which is unpaired (e.g., lacks intramolecular base pairing) but may also include a single adjoining (contiguous) paired base of a stem at either end of the loop, in forming a loop-like shape such as predicted by RNA folding algorithms. In another aspect of the invention, provided is an iNA that binds to, and internalizes into target cells, wherein the iNA comprises at least one stem-loop structure in which at least one loop portion of the at least one stem-loop structure comprises a motif selected from the group consisting of UUUCGG, UUUCGGGC, (UUUCGG)$N_m$(UUUCGG)$_n$ (SEQ ID NO:22), wherein n is a number from one to four, and between repeats of UUUCGG is one or more nucleotides N, wherein N can be any one or more of A, U, C, or G, and m is a number from 0 to 4 to signify the number of N bases, and a combination thereof. An iNA can be synthesized by any method known to those skilled in the art for nucleic acid synthesis, including but not limited to, chemical synthesis (e.g., linear synthesis, fragment synthesis (synthesis of portions) followed by assembly of the fragments to the desired complete nucleic acid molecule, or a combination thereof), enzymatic synthesis (e.g., primer extension or transcription using a polymerase), cleavage from a larger precursor, recombinant synthesis, or a combination thereof.

Two variations of the basic selection method were used in parallel to generate an iNA having binding specificity for, and mediates internalization into, target cells. Each method involved in vitro screening of complex nucleic-acid based combinatorial molecular libraries (e.g., >$10^{14}$ sequences per library) employing a selection method for cell internalizing nucleic acid molecules (see, e.g., U.S. published patent application 2009/0170711, licensed to the assignee of the present invention). Both selection processes were directed to generating an iNA which internalized into prostate cancer cells only (e.g., cell lines, or primary tumor cells). Thus, it was surprising that generated was an iNA that bound to and internalized into human cancer cells representative of various types of malignancy (e.g., in addition to prostate cancer cells), as well as to human cancer cells from various stages of malignancy. In both processes, employed was a random library of RNA molecules, with the RNA molecules comprised fixed sequences at the 5' terminus and 3' terminus of the RNA molecule which flank an internal region comprising nucleotides in a randomized sequence. While the number may vary between libraries, typically each fixed sequence comprises from about 10 to about 25 contiguous nucleotides, and the internal region comprises from about 20 to about 50 contiguous nucleotides. The library of oligonucleotides may be synthesized using any method standard in the art for nucleic acid molecule synthesis, including but not limited to chemical synthesis on an automated nucleic acid molecule synthesizer.

In the selection method, the starting library of oligonucleotides was contacted and incubated with a prostate cancer cell line. The cells were then washed, and treated with a nuclease to remove oligonucleotides which were bound to the outside of the cells. In this case, a mixture of RNases as used to digest oligonucleotides from the starting library which had not internalized into the cells. The cells were washed again, and total RNA from the treated cells was extracted. The extracted, total RNA was then reverse-transcribed, using primers specific for the fixed sequences, into DNA. These DNA templates were used to create an enriched pool of RNA molecules, through in vitro transcription, for the next round of selection. Preferably, a mutant T7 RNA polymerase was used in the transcription that allowed for the incorporation of modified nucleotides (e.g., 2'fluoro-modified pyrimidines) to enhance the stability of the enriched pool of RNA molecules in each round of selection (e.g., from nucleases that may present in the cell culture). Multiple rounds of selection are repeated. In the one variation of the selection method used, the same prostate cancer cell line (e.g., PC-3 cells) was used throughout the selection process. In the other variation of the selection method used, in repeating the multiple rounds of selection, different prostate cancer cell lines were used for different rounds. This type of selection is called a "toggle" selection. After several rounds of selection, the pool of RNA molecules can be analyzed for ability to internalize into the cells, using known methods in the art suitable for this purpose, including but not limited to quantitative PCR and flow cytometry. The pool of RNA molecules from a round of selection may also be sequenced to determine remaining diversity or convergence following a round of selection. Individual clones of interest may then be synthesized, and further characterized for properties including but not limited to binding affinity, binding specificity, and ability to be internalized. Clones of particular interest may then be further modified to be used in the present invention as an iNA.

An iNA according to the invention may be further modified to include at least one chemical modification to modulate one or more of pharmacokinetics and biodistribution of the modified iNA. For example, the iNA maybe further modified to improve in vivo stability, including but not limited to resistance to nucleases present in body fluids. Such modifications are known in the art to include one or more of capping a free end of the nucleic acid molecule to be exonuclease resistant; modifying the internucleotide linkages (e.g., by phosphorothioate or alkyl phosphate modifications); modifying nucleotides to be incorporated into the nucleic acid sequence (e.g., 2'-position sugar modifications for purines and/or pyrimidines such as O-alkyl, O-allyl, O-methyl, or halo group; 5'-position pyrimidine modifications; 8'-position purine modifications); and modifications at exocyclic amines. In one example, an iNA may be further modified to comprise at least 25% or 50% or more of the nucleotides in its sequence as having a 2'-sugar modification, such as incorporation of modified nucleotide (e.g., a 2'-sugar modification of any of the pyrimidine nucleotides may comprise a 2'fluoro modification, and/or a 2'-sugar modification of any of the purine nucleotides may comprise a 2'methoxy modification). In another example, a linker may also be used as a modification of an iNA of the invention with the objective of modulating one or more of pharmacokinetic and biodistribution properties of the iNA. To illustrate such an embodiment, the number and size of poly-ethylene glycol (PEG) molecules used to modify the iNA can vary, depending on the desired residence time in the systemic circulation or tissue following administration of the modified iNA, or a composition containing the same, for treatment of a disease.

An iNA according to the invention may be further modified to include at least one chemical modification to facilitate conjugation to an effector moiety or linker. Such modifications are known to include, but are not limited to, incorporating reactive groups either during synthesis (e.g., direct solid phase synthesis) or by post-synthesis modification. For example, during synthesis, one or more modified nucleotides may be incorporated into the iNA at a desired position, such as an allyl-containing nucleotide. In another example, a free amine is introduced at the 5' end or 3'end of the iNA by incorporating an amino-modifier phosphoramidite at the appropriate point in the solid phase synthesis. A reactive group may be incorporated post-synthesis such as by a process including, but not limited to, modifying either the 5'end or 3'end of an iNA. For example, the 5' end may be modified to include a thiophosphate (such as by using the reagent H-phosphonate derivative of 1-dimethoxytrityl 2,2'-dithiodiethanol). Additionally, carboxylic acid groups can be added to an iNA in a post-synthetic process using methods know in the art.

Drugs

An iNA of the invention may be further modified to include at least one chemical modification comprising conjugation to an effector moiety comprising a drug. The type of drug may vary depending on the target cell, and the disease to be treated. The drug may also comprise a detectable moiety (commonly termed a "theranostic"); e.g., in having pharmacological activity as well as detectable properties. For example, some drugs have, or may be modified to have, fluorescent properties which may be utilized in detection of the drug once inside the target cells. Such examples include but are not limited to doxorubicin, and cytotoxic peptides having one or more tryptophan residues. In a preferred embodiment, the drug is a cytotoxic drug, and the target cell is a precancerous cell or cancer cell. In this preferred embodiment, the preferred drugs for use with the iNA are cytotoxic drugs (cytotoxins), particularly useful for treating cancer, or precancerous conditions. In this regard, a preferred cytotoxin may be used to modify an iNA of the invention to the exclusion of cytotoxin other than the preferred cytotoxin. As will be described herein in more detail, desirably conjugation of an iNA to a drug is via a cleavable moiety such as a cleavable bond (if directly conjugated to the iNA) or cleavable linker (if the iNA is conjugated to the drug via a linker), wherein cleavage preferentially occurs in the tumor environment (e.g., nearby the tumor so as to expose the tumor to the drug, and/or inside tumor cells (intracellularly), so as to release pharmacologically active drug from iNA. For example, release of the drug nearby the tumor may be especially desirable in certain circumstances, such as to treat the tumor and/or tumor angiogenesis. General categories of cytotoxic drugs include but are not limited to DNA damaging agents and enzyme inhibitors. DNA damaging agents are known to include but are not limited to DNA cleaving agents; topoisomerase inhibitors (including but not limited to irinotecan, topotecan, camptothecin, lamellarin D, etoposide, teniposied, aurintricarboxylic acid, HU-331, and plant polyphenols (e.g., EGCG from tea polyphenols, genistein, quercetin, resveratrol)); microtubule or tubulin inhibitors ((including but not limited to vincristine, vinblastine, vinorelbine, vindesine, dolostatins (e.g., auristatin E and derivatives like monomethyl auristatin E), colchicine, taxane analogs (e.g., epothilones A, B & D), maytansinoids, crytophycins, and indibulin); and DNA intercalating agents (including but not limited to doxorubicin (adriamycin), daunorubicin, and dactinomycin). Enzyme inhibitors include dihydrofolate reductase inhibitors (including but not limited to methotrexate, and pemetrexed), topoisomerase inhibitors, and thymidylate synthase inhibitors (including but not limited to raltitrexed, pemetrexed, nolatrexed, ZD9331, and GS7904L).

Some cytotoxins, useful to modify the iNA of the present invention, may have a first reactive group which can facilitate coupling to a reactive group present on an iNA (if directly coupled) or on a linker, whereas other cytotoxins may need to be first modified themselves with a reactive group to facilitate such coupling. For example, representative cytotoxins containing a reactive group comprising a carboxyl group include but are not limited to campothecin, methotrexate, and derivatives thereof. While there are several standard methods of coupling a carboxyl group and carboxyl-reactive group, in one illustrative embodiment 1-ethyl-3-[3-dimethylaminopropyl] carbodiimide hydrochloride (EDC) is often used to couple carboxyl groups to primary amines. Also, in the presence of N-hydroxysulfosuccinimide (Sulfo-NHS), EDC can be used to convert carboxyl groups to amine-reactive Sulfo-NHS esters. Representative cytotoxins comprising a sulfhydryl group include but are not limited to esperamicin and its derivatives. While there are several standard methods of coupling a sulfhydryl group and sulfhydryl-reactive group, in one illustrative embodiment, two sulfhydryl groups can be reacted to form a disulfide bond. Also, a maleimido group may be used to conjugate to a thiol group. Representative cytotoxins comprising an amine group include but are not limited to cytabarine, mitomycins, doxorubicin, daunorubicin, and their derivatives. While there are several standard methods of coupling an amine group and amine-reactive group, in one illustrative embodiment, a carboxylic acid is converted to an amine-reactive ester (N-Hydroxysuccinimide (NHS) ester) to form an amide bond. A carbodiimide reaction may be used to link a carboxy or amino group on a drug to a carboxy or amino group on a linker or iNA. Representative cytotoxins comprising an alcohol group include but are not limited to campothecin, taxol and taxol analogs, esperamicin, vincristine, vinblastine, and their derivatives. Also, as described herein in more detail, a heterobifunctional linker may be used to couple a first reactive group (e.g., present on the cytotoxin) to a second reactive group (e.g., present on the iNA), when an iNA further comprises at least one chemical modification.

Additional examples of cytotoxins useful with an iNA of the invention include, but are not limited, to the following. Ellipticine and its derivatives (e.g., 9-hydroxylellipticine, or 6-(3-aminopropyl)-ellipticine) are potent cytotoxins that may be coupled via the 2'nitrogen to an amino acid, such as a side chain of a peptide linker. Maytansine and ansamitocin P-3 may be used themselves as cytotoxins, or may be used as precursors to synthesize maytansinoids (e.g., maytansinols; N(2')-deacetyl-N(2')-(3-mercapto-1-oxopropyl)-maytansine (DM1)) using methods known in the art. Maytansinoids may be generated which have a thiol group which can be used to couple the drug to a linker or iNA via disulfide bind formation. Maytansinol may be converted to an amine-reactive form to react with a disulfide containing carboxylic acid in a carbodiimide reaction. Calicheamicins and derivatives (e.g., N-acetyl gamma calicheamicin dimethyl hydrazide) are potent cytotoxic agents, and can be conjugated via an acid-sensitive hydrazone to a linker or iNA. The reactive hydrazide group readily reacts with aldehydes to form a hydrazone, or can be converted to a NHS-bearing amine-reactive form for coupling to an amine-containing linker or amine-containing iNA. Streptonigrin is an aminoquinone antitumour antibiotic that can be conjugate via one of its reactive groups, such as amine or hydroxyl. In addition to auristatin, dolatstatins (10 & 15) and their derivatives (e.g., synthadotin, soblidotin, cemadotin), other peptide cytotoxins include but not limited to tubulysins, *Pseudomonas* exotoxin A (or toxic fragments thereof, such as PE38 composed of amino acids 253-364 and 381-613 of *Pseudomonas* exotoxin A; and HA22-LR, containing 11 residues from domain II, and domain III, see, e.g., published U.S. Patent Application No. 20100215656), cryptophicins, HTI-286, and cyclic peptides and depsipeptides (e.g., didemnin B, kahalalide F, dehydrodidemnin B, DMMC, vitilevuamide, diazonimide, thiocoraline); which peptide cytotoxins are amenable to chemical synthesis and conjugation using standard peptide chemistries. Radioisotopes which may be used as cytotoxic moieties include but are not limited to iodine-131, yttrium-90, rhenium-188, bismuth-212, indium-11, lutetium-177, astatine-211, actinium-225, and copper-67.

Linkers

An iNA of the invention may be further modified to include at least one chemical modification comprising conjugation to a linker. The linker may comprise a cleavable linker or a non-cleavable linker, depending on the intended use. For example, if an iNA is further modified to include at least one chemical modification comprising conjugation to an effector moiety comprising a detectable moiety or a drug comprising a radioisotope via a linker, it may be desirable that the linker lack a cleavage site ("non-cleavable linker"). In an example where an iNA is further modified to include at least one chemical modification comprising conjugation to an effector moiety via a linker wherein activity of the drug or detectable moiety is optimum if released from the iNA (as compared to the activity when conjugated to an iNA via a linker), it may be desirable that the linker comprise a cleavage site ("cleavable linker"), such that the pharmacologically active drug or detectable moiety is released from the iNA to perform in the target cells. Cleavable linkers comprise one or more functional moieties that may be cleaved preferentially at a desired location, such as near or in the target cells. In the example where the target cells are tumor cells, the cleavable linker is preferentially cleaved intratumorally (e.g., one or more of: in the tumor microenvironment, and within the tumor cells). As will be described herein in more detail, illustrative examples of such cleavable linkers include but are not limited to one or more of: (i) hydrazone moieties that are stable at physiological pH and are cleaved at low pH (such as a pH encountered in lysosomes and endosomes), (ii) benzoic-imine linker moieties that are stable at physiological pH and are cleaved at a low pH (such as a pH in the range of pH 4.5-5.5 encountered in lysosomes and endosomes), (iii) a peptide sequence recognized and cleaved by lysosomal/endsomal protease (e.g., cathepsin B, furin, or a combination thereof), (iv) a peptide sequence recognized and cleaved by membrane-bound serine protease fibroblast activation protein-alpha overexpressed on the surface of tumor stromal fibroblasts but not expressed by fibroblasts or other cell types in normal (non-cancerous) tissues, and (v) a double-stranded DNA sequence which is preferentially cleaved by DNase II (an acid pH nuclease contained in endosomes and lysosomes) as compared to DNase I (contained in plasma). Thus, an iNA comprising at least one chemical modification comprising conjugation to a cleavable linker comprising one or more of a hydrazone moiety or a peptide sequence cleaved by cathepsin B, wherein the cleavable linker is also conjugated to a drug, may be used to preferentially release a drug once internalized into one or more of lysosomes and endosomes of target cells which bind and internalize the chemically modified iNA, as compared to release into the bloodstream, thereby reducing off-target effects of the drug. It has been reported that in the microenvironment of some human tumors (e.g., breast cancer), immune cells such as monocytes are stimulated by the tumor to secrete small amounts of cathepsin B in a process of promoting tumor growth, invasion, and metastasis. Similarly, the majority of epithelial tumors stimulate tumor stromal fibroblasts to produce membrane-bound serine protease fibroblast activation protein-alpha ("FAP"). Thus, in such tumor microenvironments, it may be possible that prior to internalization when bound to an iNA, a linker cleaved by cathepsin B or by membrane-bound serine protease fibroblast activation protein-alpha may release drug intratumorally. Release of drug intratumorally may treat cancer by one or more mechanisms including either directly treating tumor cells, or treating cell types other than tumor which are present in the tumor microenvironment and which support or promote tumor development (one or more of tumor growth, invasion, and metastasis).

A nucleic acid-based linker, such as comprising a nucleic acid sequence which is preferentially cleaved by DNase II as compared to DNase I, advantageously can be synthesized with the iNA in the same synthetic process, in chemically modifying the iNA, such as by a nucleic acid synthesizer. Alternatively, the nucleic acid linker is synthesized with an oligonucleotide extension (e.g., ranging from about 5 to about 15 oligonucleotides) that is complementary to an oligonucleotide extension which was synthesized onto either the 5' end or 3' end of an iNA of the invention. The complementary oligonucleotide extensions are then hybridized together in conjugating the linker to the iNA, in chemically modifying the iNA with a linker. Such hybridization can be achieved using standard conditions for hybridization, as known in the art. For example, the nucleic acid-based linker with such an oligonucleotide extension is mixed with the iNA comprising an oligonucleotide extension that is complementary to that of the linker at a ratio of twice the molar volume of the iNA with the linker in a buffer containing 50 mM $MgCl_2$. The mixture is heated at 55° C. for 10 minutes in order to denature both oligonucleotide extensions and to allow for annealing, and then cooled to 37° C. for 5 minutes in hybridizing the complementary oligonucleotide extension sequences, and in conjugating the linker to the iNA. The oligonucleotide extensions may be synthesized to incorporate modified nucleotides known in the art to be resistant to nucleases; or may themselves comprise a sequence that is preferentially cleaved by DNase II.

Illustrative examples of cleavable linkers that may be useful to chemically modify an iNA according to the invention may include but are not limited to linkers comprising the amino acid sequences or DNA sequences listed in Table 1 (single letter codes, unless otherwise indicated).

TABLE 1

| peptide sequence | enzyme/condition for preferential cleavage | SEQ ID NO: |
|---|---|---|
| GPPGP | FAP | 1 |
| GEAGP | FAP | 2 |
| GETGP | FAP | 3 |
| GESGP | FAP | 4 |
| GDTGP | FAP | 5 |
| GDSGP | FAP | 6 |
| PPGP | FAP | 7 |
| DP | acid-labile in endosonnes/lysosonnes | |
| valine-citrulline | cathepsin B | |
| phenylalanine-citrulline | cathepsin B | |
| GFLG | cathepsin B | 8 |
| FK | cathepsin B | |
| FFK | cathepsin B | |
| GFK | cathepsin B | |
| AK | cathepsin B | |
| VK | cathepsin B | |
| GFQGVQFAGF | cathepsin B | 9 |
| GFGSVQFAGF | cathepsin B | 10 |
| ALAL | cathepsin B | 11 |
| RVRR | cathepsin B and furin | 12 |
| AGNRVRRSVG | Furin | 13 |
| TRHRQPRGWEQL | Furin | 14 |
| SNSRKKRSTSAGP | Furin | 15 |
| nucleic acid sequence | | |
| (AGAGGA)n dsDNA (TCTCCT) n = a number from 1 to 5 | DNase II | 16 |
| chemical linker | | |
| benzoic-imine | —C=N — H | |
| hydrazone | R1R2C = NNH$_2$ | |

A cleavable linker, used as at least one chemical modification of an iNA for modifying an iNA with an effector moiety comprising a drug, detectable moiety, or combination thereof, may optionally further comprise a self-immolative spacer which, when present, spaces and covalently links together the linker and the drug. The self-immolative spacer, when present, is covalently linked at one of its ends to the linker (by bonding between a reactive group of the self-immolative spacer and a reactive group on the linker), and covalently linked at its other end to the effector moiety (by bonding between a reactive group of the self-immolative spacer and a reactive group on the effector moiety). This arrangement between the linker, spacer and drug is typically stable until cleavage of the cleavable linker activates the self-immolative property of the self-immolative spacer so that it spontaneously decomposes or is otherwise cleaved or released from the effector moiety without the need of an additional, separate hydrolysis or enzymatic step. In an embodiment wherein the effector moiety comprises a drug, the drug is then released from the linker in its pharmacologically active form. The self-immolative spacer may comprise a modified aminobenzyl group such as an aminobenzyl ether group, para-aminobenzyl ether, para-aminobenzyl alcohol, para-aminobenzyl-carbamoyl, or ortho or para aminobenzylacetals; a para-substituted benzyloxy-carbonyl group; a 2-aminoimidazol-5-methanol group; 4-aminobutyric acid amides or gama-aminobutyric acid or modification thereof (such as a dimethyl gama-aminobutyric acid); 2-aminophenylpropionic acid amides; and N-acylhemithioaminal derivatives. While an iNA of the invention may comprise at least one chemical modification to include a linker, and optionally to further include a self-immolative spacer, a preferred self immolative spacer may be used to the exclusion of a self-immolative spacer other than the preferred self-immolative spacer.

Linkers that are generally considered as non-cleavable include, but are not limited to a polyalkyleneglycol linker containing a chain of two or more alkylene moieties linked together by an oxygen in the form of an ether linkage (e.g., a chain comprising typically between 2 and 10 poly-ethylene glycol molecules, such as PEG-2000 Da); a thioether bond (e.g., using N-succinimidyl-4-(N-maleimidomethyl)-cyclohexane-1-carboxylate); amide (e.g., N-hydroxysuccinimide (NHS—XX—)); extended amide (e.g., N-hydroxysuccinimide polyethylene glycol (NHS-PEG); extended hydrazide linkages (e.g., hydrazide-PEG-biotin-); substituted straight or branched C1-10 alkylene chains; and one or more D-amino acids.

Detectable Moieties

An iNA of the invention may be further modified to include at least one chemical modification comprising conjugation to effector moiety comprising a detectable moiety. Conjugation may be directly between the iNA and the detectable moiety, or may be indirectly via a linker by using the linker to couple to the iNA and to the detectable moiety. The choice of the type of detectable moiety may vary as to whether the use of the modified iNA is for in vitro diagnostic methods or in vivo diagnostic methods. In a preferred embodiment, the iNA modified with a detectable moiety is used to detect the presence or absence of a target cell. In a preferred embodiment, a preferred detectable moiety may be used to modify an iNA of the invention to the exclusion of a detectable moiety other than the preferred detectable moiety. General categories of detectable moieties include but are not limited to fluorescent moieties, enzymes, chemicals, chromophores, electron transfer agents, luminescent moieties, phosphorescent moieties, magnetic moieties, radioactive moieties, affinity tags, and contrast agents (e.g., detectable by Positron Emission Tomography or Magnetic Resonance Imaging). Fluorescent moieties may include but are not limited to quantum dots or fluorescent semiconductor nanoparticles; fluorophores such as phycoerythrin, fluorescein isothiocyanate, rhodamine, Cy-chromes (e.g., Cy 3, 5, and 7), Texas Red, Alexa fluors (e.g., Alexa 350, 430, 546, 568, 594, 633, 660, and 680), and other fluorescent organic or dye labels; and fluorescent proteins such as green fluorescent protein, blue fluorescent protein, red fluorescent protein, enhanced yellow fluorescent protein, and enhanced cyan fluorescent protein; an acceptor or donor molecule of a fluorescence resonance energy transfer system (e.g., fluorescein/tetramethylrhodamine). Enzymes may include but are not limited to beta-galactosidase, horseradish peroxidase, alkaline phosphatase, and luciferase. Magnetic moieties may include but are not limited to diamagnetic, paramagnetic, or ferromagnetic materials such as beads or particles. Radioisotopes may include but are not limited to iodine-125, technetium-99, phosphorus-32, sulfur-35, gadolinium-157, indium-111, gallium-68, ruthenium-97, gallium-67, and chromium-52. Radiometals may be introduced into iNAs by chelation of the metal with a suitable binding ligand (e.g., bifunctional chelator, such as N3S-type peptide-based chelator MAG2) followed by conjugation to the iNA via a reactive group. Luminescent moieties include but are not limited to luciferin, *renilla*, luminol and other 2,3-dihydrophtahlazinediones. Affinity tags include but are not limited to polyhistidines ("His-tags"), avidin, biotin, and the like.

Uses of an iNA which is Modified to Include at Least One Chemical Modification

As described herein, in one embodiment an iNA of the invention may be further modified to include at least one chemical modification. In one embodiment, an iNA comprising at least one chemical modification comprises a conjugate of iNA with effector moiety. An iNA-effector moiety conjugate may be produced by conjugating iNA to one or more molecules of effector moiety (e.g., by coupling a reactive group of the effector moiety to a reactive group of the iNA), or by using a linker (e.g., a linker having at least two reactive groups, wherein one reactive group is coupled to a reactive group of the effector moiety, and the other reactive group of the linker is coupled to a reactive group of the iNA; or when the linker further comprises a self-immolative spacer, a reactive group of the self-immolative spacer is coupled to a reactive group of the effector moiety, and a reactive group of the linker is coupled to a reactive group of the iNA).

In one embodiment, the effector moiety comprises a drug, and preferably a cytotoxic drug, wherein an iNA-drug conjugate is used in a medicament or pharmaceutical composition for treatment of diseases involving cells to which the iNA-drug conjugate binds and internalizes. Thus, in a method of using a modified iNA comprising an iNA-drug conjugate, the modified iNA is contacted with target cells for exerting a cytotoxic effect on the target cells. Methods for determining whether an agent, such as a drug conjugate, exerts a cytotoxic effect on a cell are well known in the art. For example, apoptosis is an indicator commonly used to detect and quantitate cytotoxicity. Apoptosis can be observed by microscopic evaluation of treated cells (e.g., apoptotic cells may be characterized by membrane blebbing and condensation of cytoplasm), or be measured by quantitating DNA fragmentation (e.g., by TUNEL assay or ELISA-based assay), or determined by measuring morphological changes in the treated cells (e.g., by loss of plasma membrane activity resulting in dye uptake which can be quantitated by flow cytomety or other detection means, or by measurement of binding of annexin V to apoptotic cells such as by flow cytometry). These same techniques may be used to evaluate the cytotoxic ability of a modified iNA comprising an iNA-drug conjugate.

The invention further provides a composition, preferably a pharmaceutical composition or medicament, containing a therapeutically effective amount of an iNA-drug conjugate with a pharmaceutically acceptable carrier. A composition according to the invention may be administered once, or multiple times, as needed, to deliver a therapeutically effective amount of the composition, e.g., an amount effective to mediate modulation of disease in the individual receiving the composition. For example, an effective amount of a composition comprising an iNA-cytotoxic drug conjugate may be an amount that is cytotoxic for cells which are contacted with the composition, such as resulting from uptake of the iNA-cytotoxic drug conjugate. Such a therapeutically effective amount of the composition will depend on such factors as the mode of administration, the formulation for administration, disease to be modulated, the size and health of the individual to receive such a composition, and other factors which can be taken into consideration by a medical practitioner whom is skilled in the art of determining appropriate dosages for treatment. An amount of the composition to be administered may vary from 0.00001 grams to about 5 grams, and more typically from about 0.001 grams to about 1 gram. One skilled in the art can apply known principles and models of drug delivery and pharmacokinetics to ascertain a likely range of dosages to be tested in preclinical and clinical studies for determining a therapeutically effective amount. A pharmaceutically acceptable carrier, used in a composition of the invention, may facilitate one or more of storage, stability, administration, and delivery, of the composition. The carrier may be particulate, so that the composition may be in, for example, powder or solid form. The carrier may be in a semi-solid, gel, or liquid formula, so that the composition may be ingested, injected, applied, or otherwise administered. The carrier may be gaseous, so that the composition may be inhaled. These carriers are known in the art to include, but are not limited to, water, saline, suitable vehicle (e.g., liposome, microparticle, nanoparticle, emulsion, capsule), buffer, medical parenteral vehicle, excipient, aqueous solution, suspension, solvent, emulsions, detergent, chelating agent, solubilizing agent, diluent, salt, colorant, polymer, hydrogel, surfactant, emulsifier, adjuvant, filler, preservative, stabilizer, oil, and the like as broadly known in the pharmaceutical art.

The mode of administration of a modified iNA of the invention, or other composition comprising a modified iNA of the invention, may be any mode known in the art to be suitable for delivering a pharmaceutical composition, and particularly suitable for treating a disease such as cancer, and may include but is not limited to, intravenously, intraperitoneally, orally, subcutaneously, intramuscularly, intranasally, transdermally, by perfusion, and by peristaltic techniques. The compositions of the invention may be combined with other therapies to treat a disease. The combination therapy may be administered in concurrently, sequentially, or in regimen alternating between the composition of the invention and the other therapy. For example, in the treatment of cancer, a composition of the invention may be combined in therapy with one or more of: at least one chemotherapeutic agent, surgical removal of cancer cells, immunotherapy (e.g., including but not limited to vaccination for inducing immune response against tumor cells, or adoptive transfer of human cells activated with tumor antigen), and radiation therapy. The at least one chemotherapeutic agent, that may be used in combination therapy with a composition comprising an iNA-drug conjugate according to the invention, may include but is not limited to an alkylating agent (e.g., cisplatin), a plant alkaloid (e.g., a vinca alkaloid or taxoid), a DNA topoisomerase inhibitor (e.g., mitomycins or epipodophyllins), anti-hormonal agent, anti-folate agent (e.g., methotrexate), pyrimidine analogs, receptor blocker or antagonist or ligand (e.g., peroxisome proliferator-activated receptor-gamma (PPAR-γ) ligand, anti-VEGF antibody, anti-EGFR antibody), and cell cycle inhibitors. In one aspect, the at least one chemotherapeutic agent, used in combination therapy, is an agent to which the tumor to be treated has been determined not to be refractory. The selected combinations, timing of administration, order of administration, and dosage can be determined by, and are well within the capabilities of, a medical practitioner whom is skilled in the art for treatment of cancer. In accordance with the present methods, a composition comprising an iNA-drug conjugate is administered to an individual having, or at risk of having, a cancer comprising target cells. An "individual" is meant a mammal, and more preferably a human. As described herein in more detail, several methods known in the art can be used to determine whether or not a cancer comprises target cells. Such methods include but are not limited to flow cytometry, immunohistochemistry, polymerase chain reaction, and in vivo diagnostic imaging. The composition is administered to such individual so as to achieve a concentration of the drug, delivered by the iNA of the invention, at the area of the tumor effective to achieve the intended result, e.g., to be cytotoxic to the tumor in treating, preventing, and/or ameliorating cancer associated with expression of a cell surface molecule to which the iNA has binding specificity. Examples of cancer to be treated by the methods and compositions herein may include, but are not limited to, solid nonlymphoid tumors, leukemia, and lymphoid malignancies. The tumors may include breast cancer, lung cancer, prostate cancer, pancreatic cancer, ovarian cancer, colon cancer, rectal cancer, colorectal cancer, hepatic cancer, head and neck cancer, stomach cancer, skin cancer, cervical cancer, renal cancer, endometrial cancer, glioblastoma, Non-Hodgkin's lymphoma, Hodgkin's lymphoma, B-cell lymphomas, acute myelocytic leukemia, acute lymphoblastic leukemia, chronic lymphocytic leukemia, and chronic myelogenous leukemia. Using standard methods known in the art, effectiveness of a composition comprising an iNA-drug conjugate against a particular type or sample of tumor may be tested in standard animal models known in the art for that tumor, and/or in cell-based assays, followed by clinical trials.

In one embodiment, the effector moiety comprises a detectable moiety, wherein a composition comprising an iNA coupled to detectable moiety is used in a method for detecting the presence or absence of detectable moiety in a sample suspected of containing target cells. Such a sample may include but is not limited to cells, tissue (e.g., a biopsy, if the detection process is in vitro; or diagnostic imaging, if the detection process is in vivo), or a biological fluid (e.g., blood, plasma, serum, effusions produced by or associated with tumor, tumor extracts or homogenate or lysates, saliva, urine, and lymph). Thus, depending on the nature of the sample, the iNA could bind the cell molecule for which it has binding specificity wherein the cell molecule may present in one or more forms such as present as a cell surface molecule on target cells; and released from a cell (e.g., such as by secretion or blebbing of the cell molecule from a target cell, or such as by enzymatic treatment or solubilization (e.g., ionic and/or detergent treatment) of target cells, or as a result of being recombinantly produced by cells genetically engineered to express a cell molecule to which the nucleic acid molecule has binding specificity).

In a method of detecting the presence or absence of target cells in a sample suspected of containing target cells, the method comprises: reacting the sample with a composition comprising an iNA coupled to detectable moiety; determining the presence or absence of detectable moiety in cells contained in the sample; wherein detecting the presence of the detectable moiety in the cells is an indicator that target cells are present in the sample, and wherein absence of detecting the detectable moiety is an indicator that target cells are absent from the sample. Detecting and quantitating the amount of detectable moiety that is bound to or delivered into the sample (via the binding of the iNA, to which the detectable moiety is coupled, to the sample) can be achieved by any method known in the art including in vivo methods of detection (e.g., diagnostic imaging, including but not limited to positron emission tomography, single photon emission computed tomography, magnetic resonance imaging, radioimmunosurgery), and in vitro methods of detection (e.g., flow cytometry, immunofluorescence confocal microscopy, ELISA, bead (e.g., magnetic or plastic) sorting, immunoblot, immunostaining, immunoprecipitation assays ("immuno", in this context, means binding of the iNA to its ligand, in lieu of antibody function in the corresponding assay). The reaction conditions and incubation time may vary depending on the assay format and the type of sample analyzed, and is within the abilities of one skilled in the art. For diagnostic imaging using an iNA and a radioisotope, methods known in the art for labeling aptamers may be utilized. For example, RNA aptamers have been labeled with technetium or other radiolabels complexed with one of a variety of bifunctional chelators bearing carboxylic acid reactive groups. With respect to technetium, the complexes were formed by reduction of pertechnetate with sodium borohydride, followed by treatment with a solution of the chelator (e.g., meso-tetrakis (p-carboxyphenyl) porphyrin, mercaptoacetylglycylglycylglycylglycine (MAG3), 1,4,7,10-tetraazacyclododecane-N,N',N'',N'''-tetraaceticacid (DOTA), and a cyclen). The complexes were conjugated without isolation to a 3' amino group of the aptamer using standard chemistries.

In another example, the iNA is modified to comprise a detectable moiety suitable for positron emission tomography ("PET" imaging). In this example, one or more iNA molecules (e.g., in monovalent or multivalent format) is conjugated to a radiolabed sugar amino acid derivatives. For example, radiolabled sugar amino acid derivatives commonly used in PET imaging of tumors include, but are not limited to [$^{18}$F]Galactosamine ("[$^{18}$F]Galacto") and [$^{125}$I] Glucosamine ("[$^{125}$I]Gluco"), since sugars like galactose and glucose are important fuel sources for cancer cells. An iNA modified with a radiolabled sugar amino acid derivative can result in a targeted radiotracer useful for imaging of target cells comprising cancer cells. One illustrative example of producing such a modified iNA is by a solid phase fragment condensation method. The RNA molecule comprising the iNA is assembled on an automated nucleic acid synthesizer, and is modified at the 5'terminus with carbonyldiimidazole, ethylenediamine, and hexamethylene-1,6-diisocyanate, successively on solid phase. To this isocyanato-modified iNA is coupled an amino sugar (e.g., D-glucosamine or D-galactosamine) at room temperature. The conjugate is then treated with aqueous ammonia at 50° C. for 6 hours, and the product is then purified such as by reverse phase high performance liquid chromatography (HPLC). The amino sugar derivative of the modified iNA may then be labeled with the radioisotope using standard methods known in the art. Alternatively, a radiolabled amino sugar derivative is coupled to the isocyanato-modified iNA. The resultant modified iNA radio tracer may then be administered using methods known in the art for administering radio tracers for PET imaging.

EXAMPLE 1

In this Example, illustrated is the selection process by which a library of RNA molecules (e.g., with a diversity of about $10^{14}$ molecules per library) was selected and screened for binding and internalization into one or more human prostate carcinoma cell lines, in generating an iNA that binds to and internalizes into prostate cancer cells. The pyrimidines in the RNA used in these selections were 2'-fluoro-modified in order to protect the RNA molecules from extracellular ribonucleases (RNases), and thus make them more suitable for in vivo use. The library was comprised of RNA molecules containing a constant region (comprising nucleic acid bases in positions 1-15 of SEQ ID NO:21) flanking the 5' end of the variable region, and a constant region (comprising nucleic acid bases in positions 56-83 of SEQ ID NO:21) flanking the 3' end of the variable region, and the variable region being designated by N(40). Two variations of the basic selection method for cell internalizing nucleic acid molecules (see, e.g., U.S. published patent application 2009/0170711) were used in parallel to generate an iNA having binding specificity for prostate cancer cells. Both selection processes were directed to generating an iNA which internalized into human prostate cancer cells (e.g., cell lines, or primary tumor cells). Thus, it was surprising that generated was an iNA that bound to and internalized into human cancer cells representative of various types of malignancy (e.g., in addition to prostate cancer cells), as well as to human cancer cells from various stages of malignancy. As shown in Table 2, in one selection process, PC-3 prostate cancer cells were used. As shown in Table 3, another selection process alternated (was "toggled") between various human prostate cancer cell lines. The toggling between the various cell lines was a means to apply selective pressure for identifying RNA molecules that could internalize into human prostate cancer cell lines representing various stages of malignancy in human prostate cancer. For example, LNCaP (ATCC Number CRL-1740) prostate cancer cells represent the malignant stage of androgen dependence with high responsiveness to androgen; PC-3 prostate cancer cells (ATCC Number CRL-1435) represent the malignant stage of androgen independence; DU 145 prostate cancer cells (ATCC Number HTB-81) represent the malignant stage of metastasis to the brain; and 22Rv1 prostate cancer cells (ATCC Number CRL-2505) represent the malignant stage of androgen dependence with low responsiveness to androgen.

While Tables 2 & 3 summarize the number of rounds of selection, the RNA input at each round, and the cells used at each round, and whether or not RNase was used to remove RNA molecules bound to the cell surface, the rest of the basic selection method was essentially the same for each selection process. In each round of the selection process, approximately $4\times10^5$ cells were introduced into a well of a 6-well plate, and grown to between 50% and 80% confluency prior to treatment with the appropriate RNA input (e.g., library molecules were input for round 1; internalized RNA isolated from a previous round was the input for a subsequent round of selection). In summary, round 1 of the selection process was initiated by incubating 1 µM of the RNA library to the cells in 2 ml PBS (containing 2 mg/ml BSA, 0.2 mg/ml tRNA, 5 mM $MgCl_2$), and the cells were incubated for 4 hours at 37° C. The library was removed, cells were washed in 5 ml PBS, and then the cells were trypsinized with 2 ml Trypsin/EDTA for 5 minutes at 37° C. Trypsin was neutralized with 5 ml of complete media, and the cells were removed into a conical tube. The plate was washed with 5 ml PBS to remove any cells remaining, and these cells were combined with cells in the conical tube. The cells were pelleted by centrifugation, and then washed with 10 ml PBS. The cells in the pellet were resuspended in 0.5 ml PBS containing 20U RNase (Riboshredder™), incubated at 37° C. for 20 minutes, and then washed 3 times in 10 ml PBS. The cells were lysed with 1 ml Trizol reagent, and total RNA was extracted and purified using a supplier recommended procedure. The total RNA was reversed transcribed into cDNA using a primer specific for the conserved region of the RNA library (DPA845 ATAATCCACCTATCCCAGTAGGAGAAAT; SEQ ID NO:17) cDNA is then amplified by polymerase chain reaction (DPA843; SEQ ID NO:18; TTTGGTCCTTGTCTTATGTCCAGAATGCTAATAC-GACTCACTATAGGGAGGACGATGCGG and DPA845 ATAATCCACCTATCCCAGTAGGAGAAAT (SEQ ID NO:17)), and amplified DNA is then transcribed into RNA molecules. This completes one round of the selection process. The resultant RNA serves as the RNA input for the next round in the selection process. As noted in Tables 2 & 3, after the first few rounds of the selection process, and following application of the RNA input to the cells but prior to lysing the cells to isolate total RNA, the cells were treated with an RNase-containing solution (e.g., 20 µl of an RNase-containing solution @1U/uL in 0.5 ml PBS, with incubation for 20 minutes at 37° C.) to remove RNA input bound to the cell surface. Treatment of the cells with RNase helped to destroy RNA input bound to the cell surface so that upon recovery of total RNA and subsequent amplification of RNA input, substantially all amplified RNA input represents RNA input that has been internalized into the cells. As noted in Tables 2 & 3, as the selection process progresses through multiple rounds, the amount of RNA input may be decreased so as to increase the selection pressure for internalization. Typically, after several rounds of selection, and prior to use for initiating the next round of selection, the resultant RNA molecules were cloned and sequenced for comparing the individual RNA molecules from that round to detect convergence of nucleotide sequences (which, when detected, is an indication that the selection process is approaching or has reached completion). As shown in Tables 2 & 3, the selection process was completed after round 9 and round 14, respectively.

TABLE 2

Selection on PC-3 human prostate cancer cells

| Round # | Cell Type | RNA input concentration | RNase treatment |
| --- | --- | --- | --- |
| 1 | PC-3 | 1 uM | − |
| 2 | PC-3 | 500 nM | − |
| 3 | PC-3 | 500 nM | + |
| 4 | PC-3 | 250 nM | + |
| 5 | PC-3 | 250 nM | + |
| 6 | PC-3 | 250 nM | + |
| 7 | PC-3 | 250 nM | + |
| 8 | PC-3 | 250 nM | + |
| 9 | PC-3 | 250 nM | + |

TABLE 3

Toggle Selection using various human prostate cancer cells

| Round # | Cell Type | RNA input concentration | RNase treatment |
| --- | --- | --- | --- |
| 1 | LNCaP | 1 uM | − |
| 2 | PC-3 | 500 nM | − |
| 3 | PC-3 | 500 nM | − |
| 4 | PC-3 | 500 nM | + |
| 5 | PC-3 | 500 nM | + |
| 6 | PC-3 | 500 nM | + |
| 7 | DU 145 | 500 nM | + |
| 8 | DU 145 | 250 nM | + |
| 9 | 22Rv1 | 250 nM | + |
| 10 | 22Rv1 | 250 nM | + |
| 11 | 22Rv1 | 250 nM | + |
| 12 | PC-3 | 250 nM | + |
| 13 | PC-3 | 250 nM | + |
| 14 | PC-3 | 250 nM | + |

Figure 1B:
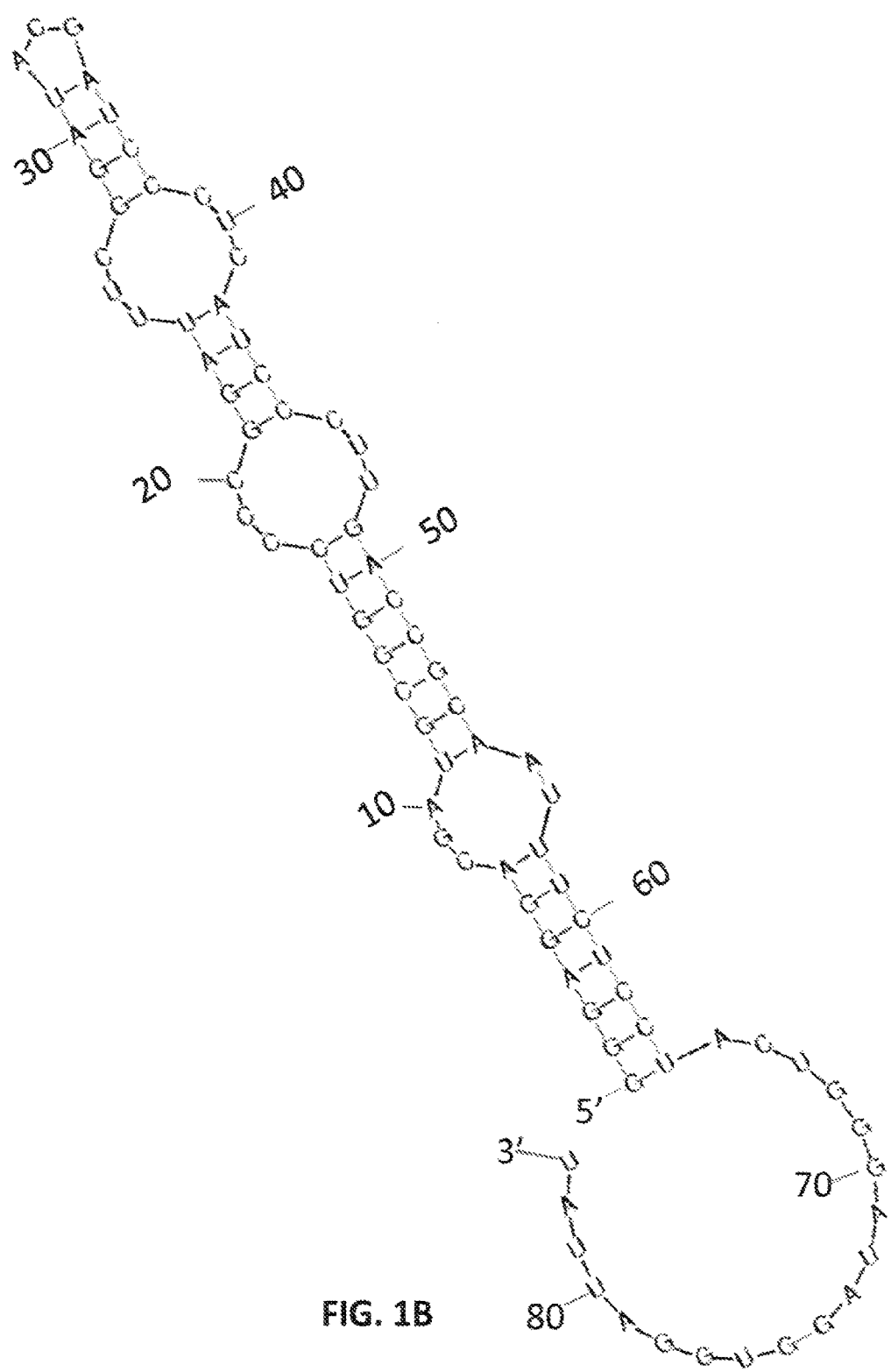

Upon analysis of the variable regions of nucleic acid sequences from clones isolated from rounds 7 and 9 of the selection process with PC-3 human prostate cancer cells and from clones isolated from round 14 of the toggle selection process, it was surprising to observe that not only was there evidence of a convergence of sequence shared by both selection processes, but also that clones of identical sequence were isolated from both selection processes (see, Tables 4 and 5). This was a surprising finding, because used in the toggle selection process, but not in the other selection process, was a variety of human prostate cancer cell lines representing various stages of malignancy in human prostate cancer. Illustrative examples of the of the iNAs isolated from the aforementioned selections, for an iNA capable of internalizing into human prostate cancer cells representing various stages of malignancy, are shown in Table 4; wherein nucleic acid sequences comprising SEQ ID NOs:19 and 20 represent the variable regions from clones with binding affinity to human prostate cancer cells; and a nucleic acid sequence comprising SEQ ID:21 represents the RNA library constant regions, with a constant region (comprising nucleic acid bases in positions 1-15 of SEQ ID NO:21) flanking the 5' end of the variable regions, and a constant region (comprising nucleic acid bases in positions 56-83 of SEQ ID NO:21) flanking the 3' end of the variable regions, and the variable regions being designated by N(40) in Table 4 (nucleic acid bases in positions 16-55 of SEQ ID NO:21). Some of the iNA variable region sequences listed in Table 4 represent clones appearing multiple times in a selection process. It is understood by those skilled in the art that the variable regions may be flanked by constant regions other than those comprising the constant regions depicted in SEQ ID NO:21, while still retaining binding activity for the cell surface molecule on target cells for which nucleic acid sequences represented by SEQ ID NOs:19 and 20 have binding affinity, and the ability to mediate internalization into the target cells (see, e.g., Example 3, herein). Unless noted otherwise, the individual sequences listed below in Table 4 are represented in 5' to 3' orientation, and were derived from clones wherein all the cytidine triphosphate and uridine triphosphate are 2' fluoro.

predicting secondary structure of RNA molecules, it is apparent that an iNA of the invention comprises at least one stem-loop structure comprising one or more conserved motifs comprising a nucleotide sequence, 5' to 3' notation, comprising one or more of UUUCGG, and $(UUUCGG)N_m$ $(UUUCGG)_n$ (SEQ ID NO:22). Preferably, a conserved motif is present in at least one loop portion, or in at least one loop portion and a part of a stem portion connected to (e.g., the base-paired nucleotides from which the loop extends) such loop portion, of the stem-loop structure. As shown in FIG. 1 A, the conserved motif comprises nucleotides that appear as adjoining or consecutive nucleotides in the loop portion of a stem-loop structure, or in a loop portion and part of a stem portion connected to such loop portion (see, e.g., FIG. 1B (D11)). Also shown in Table 4, and FIG. 1A, the conserved motif UUUCGG can appear more than once in the structure of, and the sequence of, an iNA.

EXAMPLE 2

In this Example, illustrated is characterization of clones chosen for further analysis from the selection process outlined in Example 1 herein. Additionally, illustrated are iNAs that bind to and internalize into target cells, which are further modified to include at least one chemical modification comprising conjugation to effector moiety comprising a detectable moiety. In this illustration of the invention, the iNA is further modified to comprise a detectable moiety comprising a fluorescent moiety. In this example, the fluorescent moiety comprised Alexa 647. Clones were chosen for further analysis from the selection process outlined in Example 1 herein on the basis of sequence convergence. The selected clones, and molecules of iNA, were modified to further comprise Alexa 647 by the following methods. Several clones whose sequences appeared multiple times in sequence analysis were transcribed with a 3'-extention

TABLE 4

| SEQ ID No: ; and clone id | 5' to 3' Nucleic Acid Sequence | Selection Process |
|---|---|---|
| 19; E3 | UACUUUCGGGCUUUCGGCAACAUCAGCCCCUCAGGACGCA | Round 9 PC-3 |
| 19; C9 | UACUUUCGGGCUUUCGGCAACAUCAGCCCCUCAGGACGCA | Round 14 toggle |
| 20; D11 | UCCCCGGAUUUCGGAUACGAUCCCUCAUCCCUUGACCGCA | Round 14 toggle |
| 21 | GGGAGGACGAUGCGGNNNNNNNNNNNNNNNNNNNNNNNNN NNNNNNNNNNNNNNNNNNAUUUCUCCUACUGGGAUAGGUGG AUUAU | library |

As shown in Table 4, analysis of these clones revealed unique random region sequences containing conserved motifs, indicated by underlining. These conserved motifs comprise the following. In its most basic form, a conserved motif comprises, in a 5' to 3' direction, the contiguous sequence consisting of UUUCGG. In expanded form, the conserved motif comprises $(UUUCGG)N_m(UUUCGG)_n$ (SEQ ID NO:22), wherein n is a number from one to four, and between repeats UUUCGG is one or more nucleotides N, wherein N can be any one or more of A, U, C, or G, and m is a number from 0 to 4 to signify the number of N bases (see, e.g., Table 4). Using RNA folding algorithms standard in the art (e.g., RNA folding by m-fold algorithm) for (CACGAGAGGUCCUCCGGAAGC; SEQ ID NO:23), hybridized to a DNA oligo labeled with Alexa647 (ALX647-GCTTCCGGAGGACCTCTCGTG; SEQ ID NO:24), and applied to cells for analysis.

In illustrating a screening process for internalization, from clones selected for further analysis from the selection process, a flow cytometric-based assay for binding and/or internalization was utilized. Typically, the assay was performed by incubating 200 nM of each clone with $5 \times 10^5$ target cells in 100 ul PBS containing 0.5% bovine serum albumin (BSA) in a 13 mm tube for 2 hours @ 37° C. A first portion of the cells was then treated with RNAse to remove any of the clone remaining bound to the surface of the cells, so as to allow detection and quantitation of internalized clone (i.e., measuring internalization). In parallel, a second portion of the cells was treated with PBS containing 0.5% BSA (lacking added RNase activity to enzymatically cleave cell surface proteins), so as to allow detection and quantitation of clone remaining bound to the cell surface, as well as internalized clone (i.e., measuring binding and internalization). Following further washes with phosphate-buffered saline, the cells were fixed in 1% formaldehyde and then subjected to analysis on a flow cytometer using commercially available analysis software. In performing analyses by flow cytometry, several assay controls were used. As an assay control representing either no or background (e.g., non-specific) internalization, an RNA molecule resulting from a selection process for binding a molecule not detectably expressed on target cells was used. The assay control RNA molecule was further modified with Alexa 647, and then used for further characterization of clones from the selection process described herein. For ease of description and reference for this Example, this assay control RNA molecule is referred to herein as Negative Control 1 (see, e.g., Table 5). As an additional assay control that represents either no or background internalization, used was an RNA molecule from the starting library which was chosen from the library prior to beginning a selection method described herein, and that was further modified with Alexa 647. This assay control RNA molecule is referred to herein as Negative Control 2 (see, e.g., Tables 5, 7, and 8). Additionally, fluorescence of unstained cells was measured, as a control, to quantitate any background fluorescent properties of the cells themselves as encountered in analyses by flow cytometry ("Unstained"), as opposed to fluorescent signal mediated by the RNA molecules further modified to include Alexa 647. Shown in Table 5 are the results of analyses by flow cytometry in which measured and quantitated was the ability of clones, selected on the basis of sequence convergence, to internalize into target cells represented by human prostate cancer cell line PC-3. The units of fluorescence in Table 5 represent mean fluorescence ("Mean"). The fold increase (determined by dividing the mean fluorescence of a clone by the mean fluorescence of unstained cells) is an indicator of the ability of a clone, or a clone which has been further modified to include an effector moiety, to internalize into the target cells (Table 5; "Fold Increase").

TABLE 5

Internalization screening assay in PC-3 cells

| | Mean | Fold Increase |
|---|---|---|
| Unstained | 79.9 | — |
| Negative Control 1 | 138 | 1.7 |
| Negative Control 2 | 136 | 1.7 |
| E3 (SEQ ID NO: 39) | 665 | 8.3 |
| D11 (SEQ ID NO: 38) | 460 | 5.8 |

The results shown in Table 5 illustrate that, as shown by a flow cytometric-based screening assay for internalization, clones E3 and D11 are iNA, RNA molecules which mediate internalization into cells. As described in more detail in Example 1 herein, the clones most efficient in mediating internalization have in common a conserved motif consisting of 5' UUUCGG 3'. These results also show that iNA of the invention can be further modified with at least one chemical modification comprising an effector moiety comprising a detectable moiety, and such chemically modified iNA can then be used in a method for detecting the presence or absence of target cells in a sample suspected of containing target cells. Further illustrated, in this Example, is a method of specifically delivering an effector moiety into cancer cells, comprising the steps of contacting the cancer cells with an iNA which is coupled to an effector moiety, wherein the iNA specifically binds to a cell surface molecule for which the iNA has binding specificity, wherein the effector moiety is delivered into the cancer cells.

EXAMPLE 3

For optimal synthesis conditions for iNAs comprising at least one stem-loop structure comprising one or more of conserved motifs and having the ability to bind and internalize in target cells, it is desirable that identified is a minimum RNA sequence requirement for binding and internalizing into target cells. For example, as shown in FIGS. 1 A & B, the secondary structure of an iNA of the invention is predicted by the MFOLD RNA folding algorithm to comprise a stem-loop structure comprising multiple loops and stems, wherein at least one stem-loop structure comprises a conserved motif of one or more of UUUCGG comprising nucleotides that appear as adjoining or consecutive nucleotides in the loop portion of the stem-loop structure (see, e.g., FIG. 1A (E3)), or in a loop portion and part of a stem portion connected to such loop portion of the stem-loop structure (see, e.g., FIG. 1B, (D11)). In one aspect of the invention, as shown in FIG. 1A and FIG. 1B, the at least one loop portion, containing the conserved motif of an iNA of the invention, of a stem-loop structure (containing two or more loop portions) is a loop portion adjoined or contacted by two separate stem portions (i.e., the loop portion is a loop portion internal to the stem-loop structure), as distinguished from a loop portion at the terminus of a stem-loop structure adjoined or contacted by only one stem portion (as predicted by the RNA folding program).

Figure 2A:
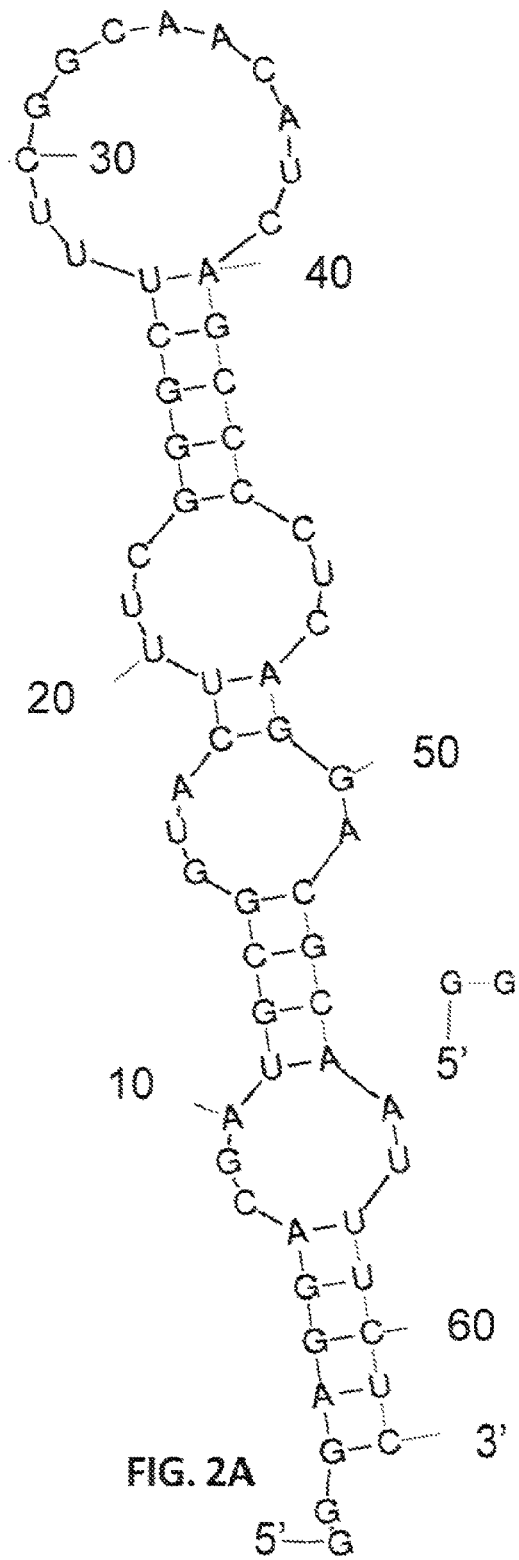
Figure 2B:
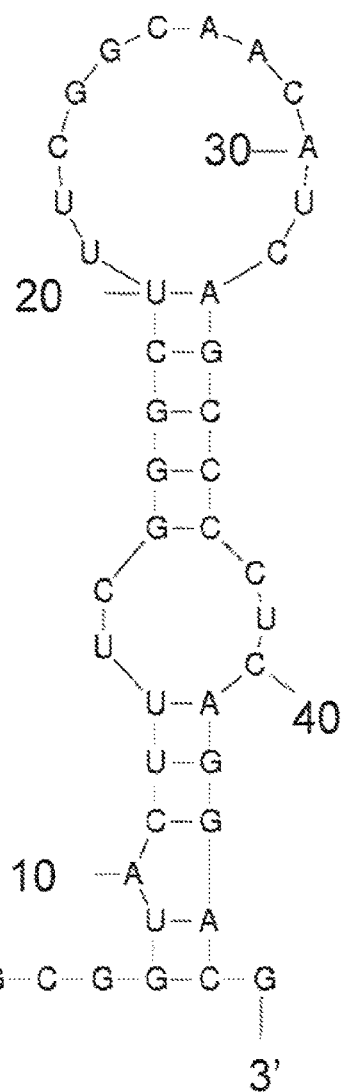
Figures 2C, 2D:
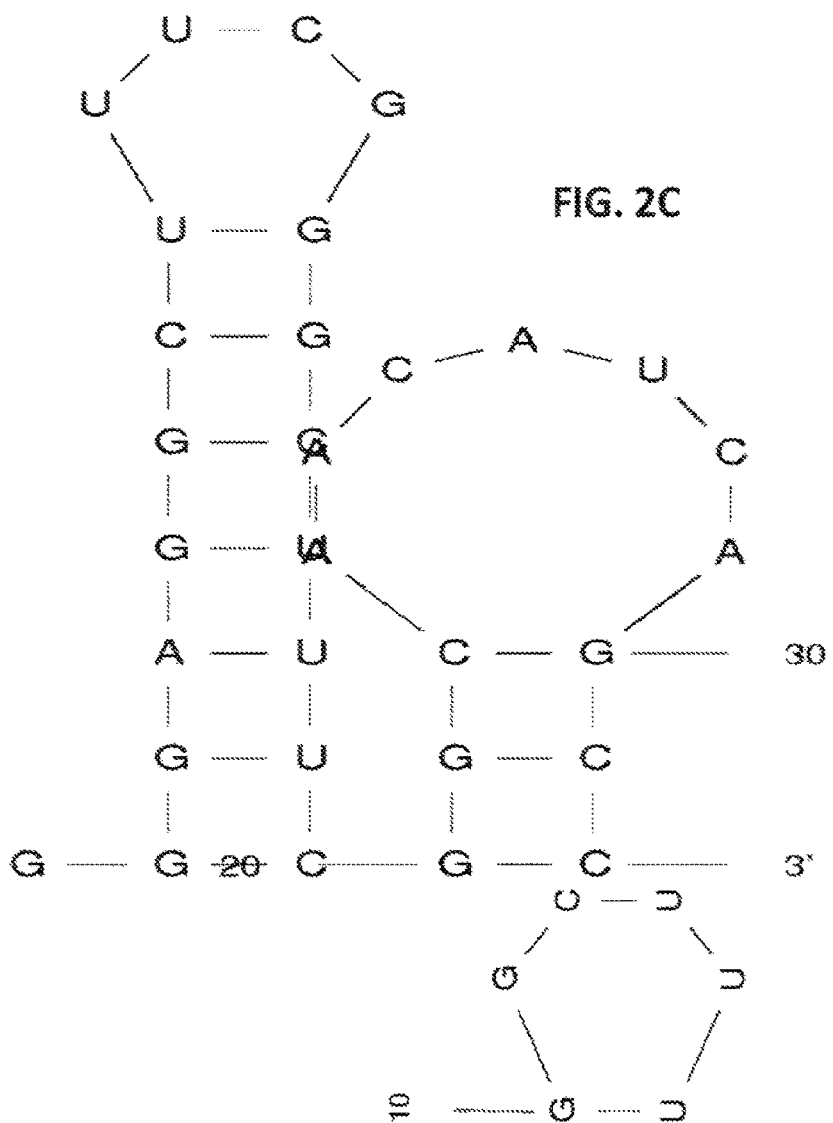

To illustrate modification of an iNA according to the invention by truncations, a representative iNA shown in Table 4 and FIG. 1A was subjected to truncations of either or both of the 5' constant region or the 3' constant region. In the design of the truncated RNA molecules, some additional bases were added for one or more of (a) increasing the length of the stem structure adjoining the loop comprising the conserved motif in efforts to stabilize the structure as a stem loop structure (e.g., by adding one or more bases on the 5' end of the relevant stem structure which could Watson-Crick base pair with one or more bases added to the 3' end of the relevant stem structure); and (b) adding initiator sequences for T7 polymerase, in the case that it was desired to produce the RNA molecule by transcription (see, e.g., FIG. 3, the last 5 nucleotides, CACCC, on the 3' end for each nucleic acid sequence shown). However, as apparent to one skilled in the art, the initiator sequences can be removed if the molecule is to be chemically synthesized versus enzymatically synthesized. The nucleotide sequences of the resultant truncations comprise 62 bases, 45 bases, 32 bases, and 22 bases, respectively, of the starting iNA sequence comprising a sequence of SEQ ID NO:39 (see, Table 6, with a conserved motif illustrated by underlined sequence). As shown in FIGS. 2 A-D, MFOLD RNA folding algorithms predicted secondary structures for each truncation illustrated in Table 6 to comprise at least one stem loop structure comprising at least one conserved motif (as described in Example 1 herein). Unless noted otherwise, the individual sequences listed below in Table 6 are represented in 5' to 3' orientation, and were derived from RNA molecules comprising truncations of an iNA of the invention, wherein all the cytidine triphosphate and uridine triphosphate are 2' fluoro.

TABLE 6

Truncations of iNA (E3)

| Clone id & SEQ ID No: | 5' to 3' Nucleic Acid Sequence |
|---|---|
| E3; SEQ ID NO: 39 | GGGAGGACGAUGCGGUAC<u>UUUCGGG</u>C<u>UUUCGG</u>CAACAUCAGCCCCUCAGGACGCAAUUUCUCCUACUGGGAUAGGUGGAUUAU |
| E3-62; SEQ ID NO: 25 | GGGAGGACGAUGCGGUAC<u>UUUCGGG</u>C<u>UUUCGG</u>CAACAUCAGCCCCUCAGGACGCAAUUUCUC |
| E3-45; SEQ ID NO: 26 | GGGUGCGGUAC<u>UUUCGGG</u>C<u>UUUCGG</u>CAACAUCAGCCCCUCAGGACG |
| E3-32; SEQ ID NO: 27 | GGGAGGC<u>UUUCGGG</u>C<u>UUUCGG</u>CAACAUCAGCC |
| E3-22; SEQ ID NO: 28 | GGGAGGCUGGGC<u>UUUCGG</u>CAAC |

The truncations, illustrated in Table 6, were each further modified with a detectable moiety, Alexa 647, and analyzed by a flow cytometric-based screening assay for internalization using the methods outlined in Example 2, to determine minimal sequences that maintain the full ability to internalize into human prostate cancer cells. Shown in Table 7 are the results of analyses by flow cytometry in which measured and quantitated was the ability of each truncation to internalize into target cells represented by human prostate cancer cell line PC-3. The units of fluorescence in Table 7 represent mean fluorescence intensity ("Mean"). The fold increase (determined by dividing the mean fluorescence intensity of a truncation by the mean fluorescence intensity of unstained cells) is an indicator of the ability of a truncation, or a truncation which has been further modified to include an effector moiety, to internalize into the target cells (Table 7; "Fold increase").

TABLE 7

Internalization screening assay in PC-3 cells

|  | Mean | Fold increase |
|---|---|---|
| Unstained | 80.2 | — |
| Negative Control 1 | — |  |
| Negative Control 2 | 129 | 1.6 |
| E3 | 907 | 11.3 |
| E3-62 | 858 | 10.7 |
| E3-45 | 690 | 8.6 |
| E3-32 | 944 | 11.8 |
| E3-22 | 80.7 | 1.0 |

The results in Table 7 illustrate that, as shown by a flow cytometric-based screening assay for internalization and using a nucleic acid sequence comprising SEQ ID NO:39 (E3) as an illustration, following initial selection for iNAs, such iNAs may be further reduced in length and still maintain the ability to internalize into target cells; and that such truncated iNAs may comprise at least one chemical modification (e.g., to further comprise an effector moiety) and retain the ability to internalize into target cells. As described in more detail in Example 1 herein, these truncated iNA have in common a conserved motif comprising one or more 5' UUUCGG 3'. The nucleic acid sequences of the truncated iNA, comprising one or more conserved motifs, can be synthesized by conventional synthetic techniques (e.g., linear synthesis) or biochemical techniques (e.g., recombinant techniques, or enzymatic processes such as transcription). Further, the constant regions of the iNA and variable region of the iNA may further comprise a chemical modification comprising one or more deletions, substitutions or additions of nucleotides, provided the correct folding of the iNA is maintained such that the conserved motif contained in a stem-loop structure demonstrates binding and internalization into target cells. Using conventional RNA-folding algorithms (e.g., MFOLD algorithm) known in the art, and the assays described herein in Examples 1-3, one skilled in the art would be able to predict with reasonable chance of success on which such alterations of one or more of the constant region of the iNA, or variable region surrounding the conserved motif of the iNA, will affect or not affect the appearance of the conserved motif in the loop portion of such stem-loop structure, as well as affect or not affect the binding and internalization ability of resultant modified iNA.

EXAMPLE 4

In this Example, illustrated is the conserved motif's role in the iNA's binding specificity to its ligand, and resulting internalization. A series of seven mutants were created by site-directed mutagenesis, using the Kunkel method and mutagenic oligonucleotides containing the desired base substitutions so that the specific mutations were inserted into the desired location in the iNA nucleic acid sequence (see, e.g., FIG. 3). Mutated were different portions of a loop portion, of a stem-loop structure, containing a conserved motif (UUUCGG) expected to be responsible for function (binding to the ligand and subsequent internalization) of the iNA (see, e.g., FIG. 3, mutants 2-8). The mutations were designed such that, as predicted by RNA-folding algorithms, maintained is the stem-loop structure; i.e., mutations did not result in loss of the loop portion being mutated. Also, as an assay control, a mutation was made in a loop of the iNA which was not expected to be responsible for the iNA's function (see, e.g., FIG. 3, mutant 1). Using the methods essentially as described herein in Examples 1 and 2, a flow cytometric-based screening assay for internalization was used to determine the effect of the mutation the ability to internalize into human prostate cancer cells. Shown in Table 8 are the results of analyses by flow cytometry in which measured and quantitated was the ability of each mutant to internalize into target cells represented by human prostate cancer cell line PC-3. The units of fluorescence in Table 8 represent mean fluorescence intensity ("Mean"). The fold increase (determined by dividing the mean fluorescence intensity of a mutant by the mean fluorescence intensity of unstained cells) is an indicator of the ability (or inability) of a mutation in the iNA to internalize into the target cells (Table 8; "Fold increase").

TABLE 8

Internalization screening assay of mutants in PC-3 cells

| | Mean | Fold increase |
|---|---|---|
| Unstained | 86.4 | — |
| Negative Control 2 | 158 | 1.8 |
| E3-45 (SEQ ID NO: 26) | 470 | 5.4 |
| mutant 1 (SEQ ID NO: 29) | 405 | 4.7 |
| mutant 2 (SEQ ID NO: 30) | 127 | 1.5 |
| mutant 3 (SEQ ID NO: 31) | 142 | 1.6 |
| mutant 4 (SEQ ID NO: 32) | 176 | 2.0 |
| mutant 5 (SEQ ID NO: 33) | 164 | 1.9 |
| mutant 6 (SEQ ID NO: 34) | 167 | 1.9 |
| mutant 7 (SEQ ID NO: 35) | 153 | 1.8 |
| mutant 8 (SEQ ID NO: 36) | 130 | 1.5 |

Figure 3:
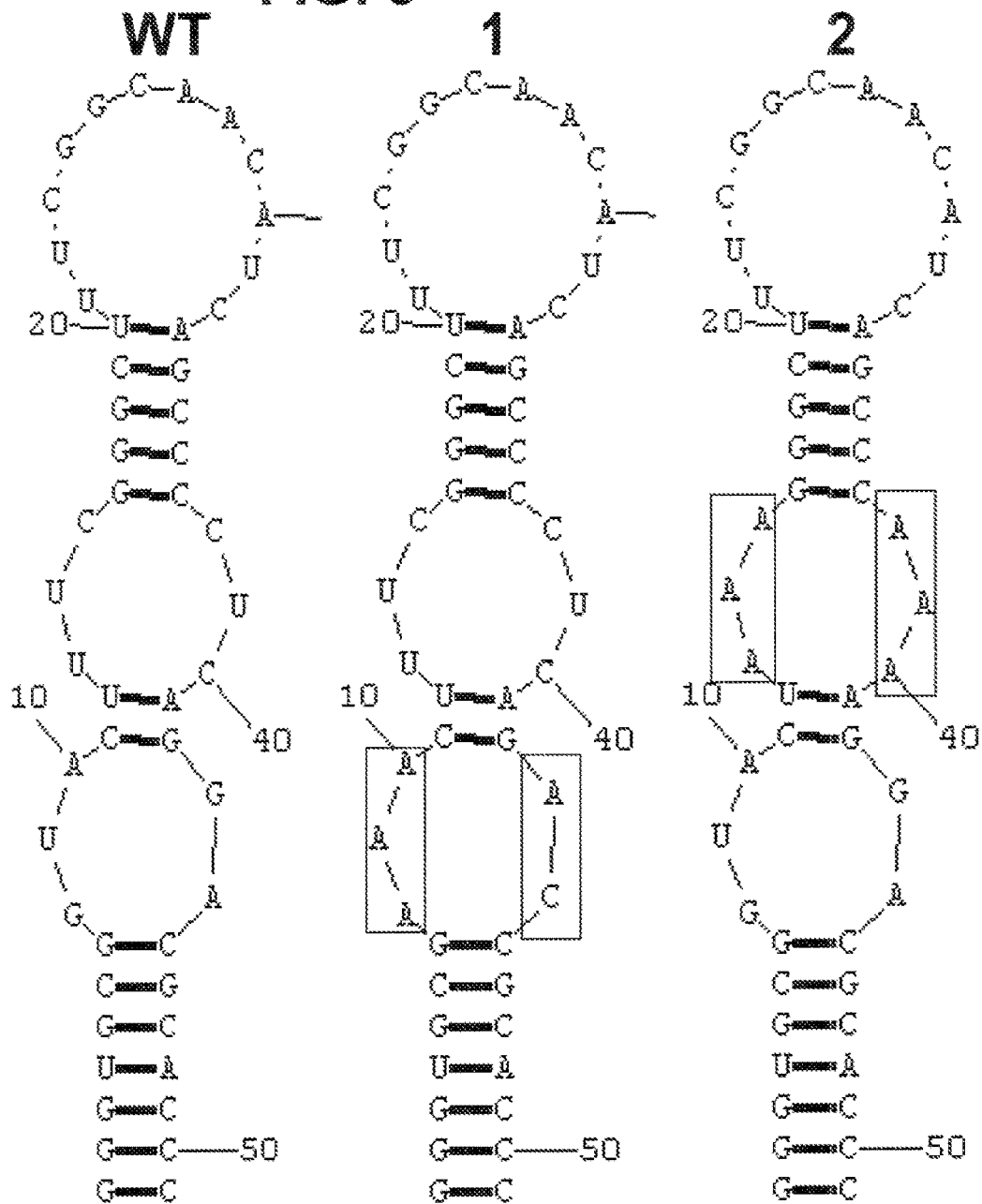
FIG. 3 is a secondary structure schematic for an iNA comprising a nucleotide sequence comprising SEQ ID NO:26; and for mutants 1-8 of such iNA comprising nucleotide sequences of SEQ ID NOs:29-36, respectively.
Figure 3:
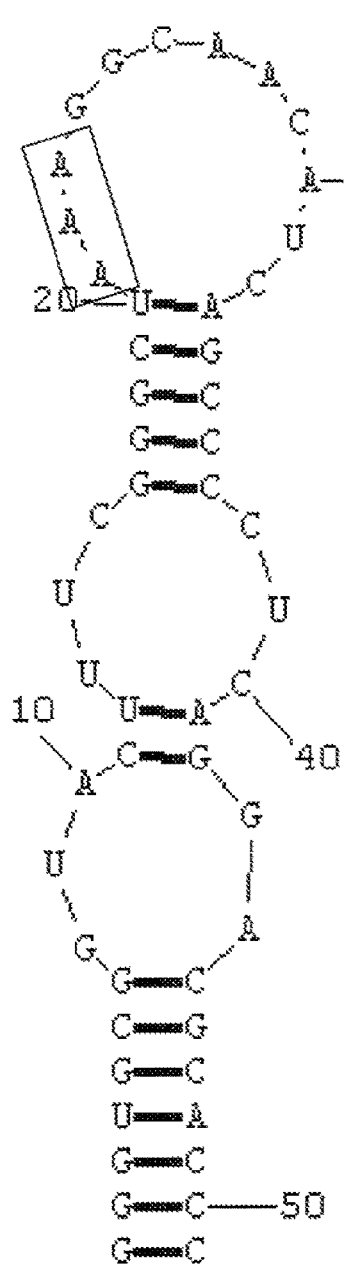
Figure 3:
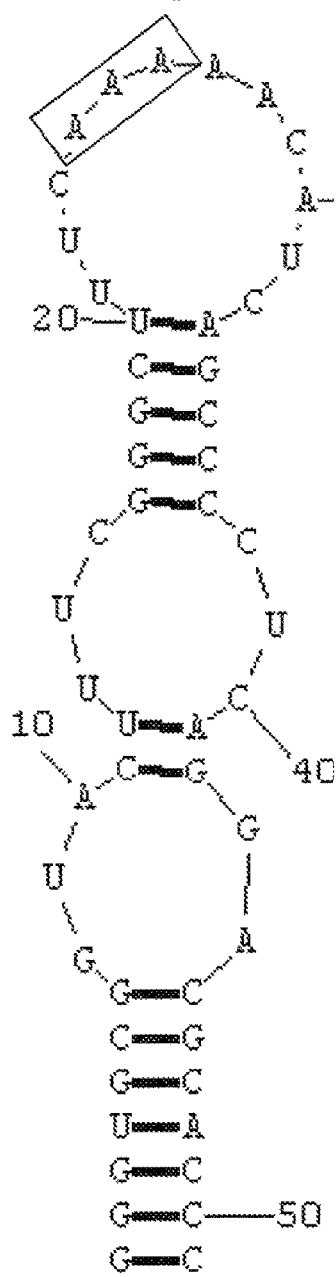
Figure 3:
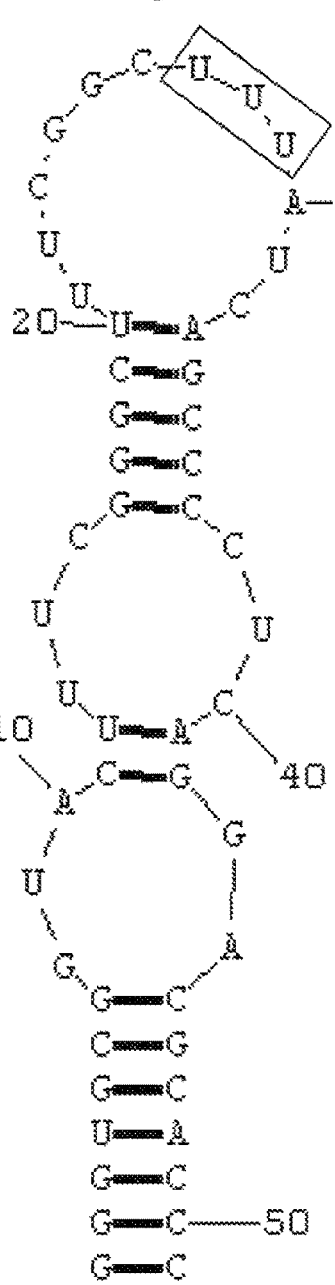
Figure 3:
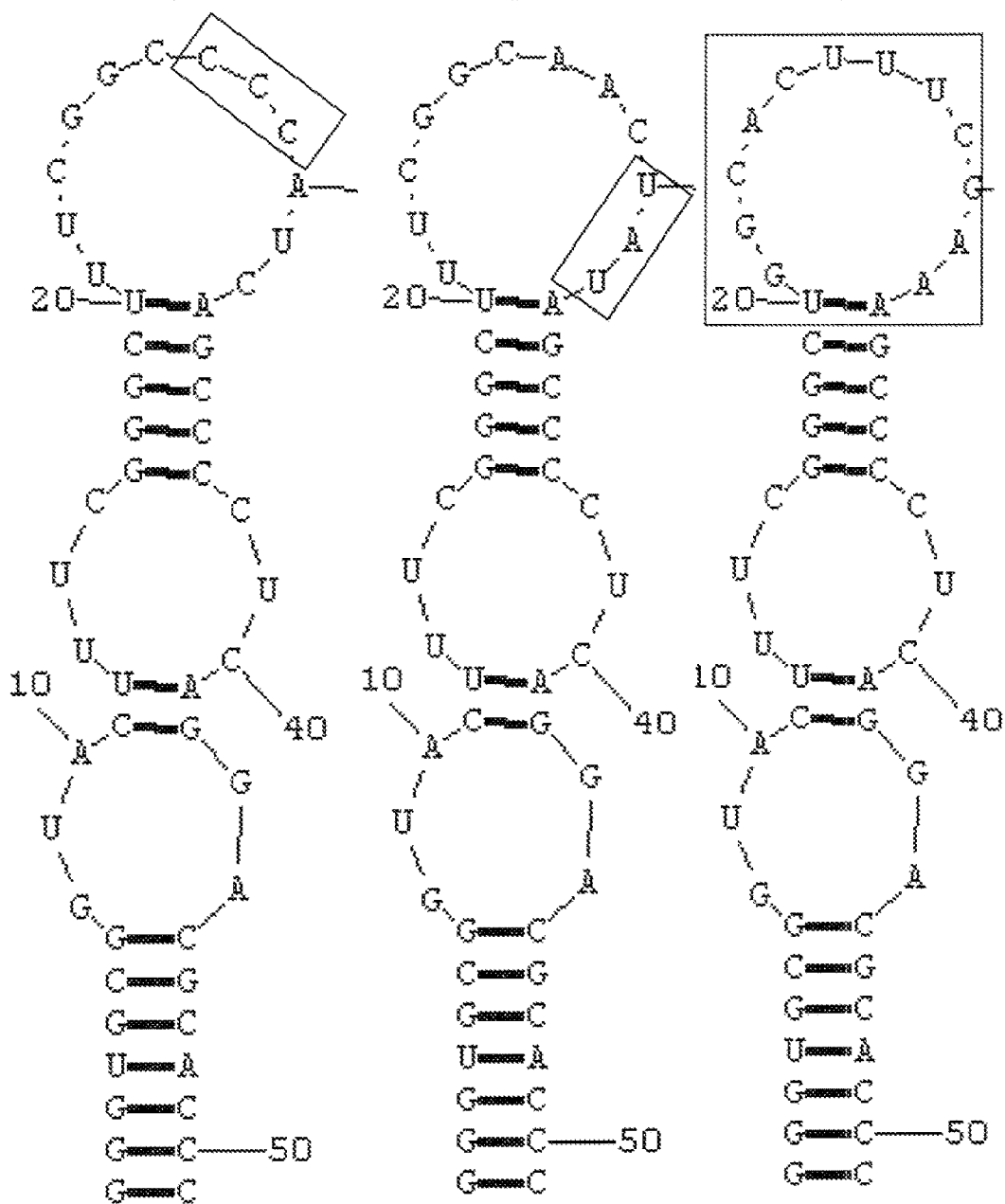

As shown in Table 8, and the assay control (FIG. 3, mutant 1) mutating a loop portion of a stem-loop structure wherein the loop portion does not contain the conserved motif UUUCGG, results in an ability to internalize equally, as compared to that of the wildtype (unmutated) iNA (E3-45; FIG. 3, WT, SEQ ID NO:26). However, mutating the conserved motif, UUUCGG, in either of the loop portions of a stem-loop structure ((see, e.g., mutants 2, 3, and 4, FIG. 3), results in loss of the ability to bind and internalize (see, e.g., mutants 2, 3, and 4, Table 8) as compared to that of the wildtype iNA (E3-45; FIG. 3, WT, SEQ ID NO:26, Table 8). Mutating the loop portion of the stem-loop structure to a sequence consisting of 5' to 3' UUUCGAG (see, e.g., mutant 8, SEQ ID NO:36, and FIG. 3) also resulted in loss of binding and internalization as compared to that of the wildtype iNA (E3-45; FIG. 3, WT, SEQ ID NO:26, Table 8). The lack of binding and internalization by mutant 8 is evidence that the iNA of the invention, having at least one conserved motif having a nucleotide sequence of at least the contiguous bases UUUCGG appearing in at least one loop portion of a stem-loop structure, is functionally and chemically (as by nucleotide sequence) different than an aptamer described by Jeong et al. (*Biochem. Biophys. Res. Commun.* 281:237-243, 2001) having a nucleotide sequence of SEQ ID NO:37 and containing a UUUCGA in a loop portion of a stem-loop structure. By RNA folding algorithms, the aptamer having a nucleotide sequence of SEQ ID NO:37 contains a UUUCG sequence in a terminal loop portion (adjoined or contacted by only one stem portion) of the stem-loop structure of the aptamer, as distinguished from having at least one conserved motif comprising UUUCGG in at least one loop portion comprising an internal loop portion (adjoined or contacted by two separate stem portions) of a stem-loop structure demonstrated by an iNA (by itself or containing at least one modification) of the invention (see, e.g., FIGS. 1A and 1B); thereby also demonstrating a structural difference when compared.

EXAMPLE 5

In this Example, illustrated is the ability of an iNA of the invention to bind and internalize into human prostate cancer cell lines representing various stages of malignancy in human prostate cancer, and, surprisingly, to bind and internalize into human cancer cells representative of various types of malignancy (e.g., prostate cancer, breast cancer, chronic myelogenous leukemia, B cell lymphoma, glioblastoma multiforme, epidermoid carcinoma, but not detectably to human cells of normal (non-malignant) tissue tested. Using the methods essentially as described herein in Examples 1 and 2, a flow cytometric-based screening assay for internalization was used to determine the ability of an iNA of the invention to internalize into cells from various types of malignancy, as well as into cells isolated from healthy (nonmalignant) human tissue. Shown in Table 9 are the results of analyses by flow cytometry in which measured and quantitated was the ability of the iNA to internalize into cells from various malignant or nonmalignant tissues. Measured was the mean fluorescence intensity for each cell type contacted with the relevant iNA (e.g., D11 or E3). The fold increase (determined by dividing the mean fluorescence intensity of a cell type using the relevant iNA by the mean fluorescence intensity of unstained cells) is an indicator of the ability (or inability) of an iNA of the invention to internalize into such cells (Table 9; "Fold increase"). An assay control, not known to have cell specific binding and internalization activity ("negative control"), was also tested in some cases (Table 9, "NC"). This negative control can be used to represent non-specific binding and/or internalization (e.g., via a mechanism such as pinocytosis) of a nucleic acid molecule to a cell type.

TABLE 9

Binding and Internalization of iNAs for other cells

| Cell type and derivation | D11 Fold increase | E3 Fold increase | NC Fold increase |
|---|---|---|---|
| malignant | | | |
| K562 human chronic myelogenous leukemia | 19.0 | 23.2 | 2.1 |
| A431 human epidermoid carcinoma | | 6.9 | 2.5 |
| PC3 Bone metastatic lesion of human Prostate adenocarcinoma | 5.8 | 9.4 | 1.6 |
| DU145 human prostate cancer, metastatic | | 6.1 | 1.9 |
| 22Rv1 Human prostate xenografts in mice | | 14.8 | 2.8 |
| LNCaP lymph node metastatic lesion of human prostate adenocarcinoma | | 6.1 | 2.4 |
| A549 human lung adenocarcinoma | 3.2 | 3.7 | 1.7 |
| MCF7 human breast adenocarcinoma | 11.7 | 31.0 | 3.0 |
| T47D human ductal breast epithelial tumor cell line | | 25.8 | 1.9 |
| SKBR3 human breast adenocarcinoma | | 14.3 | 1.6 |
| HCC1937 human, triple negative, primary breast carcinoma | | 11.8 | 2.2 |

TABLE 9-continued

Binding and Internalization of iNAs for other cells

| Cell type and derivation | D11 Fold increase | E3 Fold increase | NC Fold increase |
|---|---|---|---|
| HS578T Human, triple negative, highly metastatic breast carcinoma | | 9.8 | 3.5 |
| HCC1143 human, triple negative, breast carcinoma transformed cells | | 2.1 | 9.0 |
| WIL-2 B lymphoblastoid cell line transformed with Epstein Barr virus, from human hereditary spherocytic anemia nonmalignant | 11.4 | 20.6 | 2.6 |
| PrEC human primary prostate epithelial cells | 2.7 | 2.6 | 2.8 |
| PBMC (unstim) human, unstimulated peripheral blood mononuclear cells | | 2.4 | 2.1 |
| human primary mammary epithelial cells | | 5.7 | 4.8 |

Further illustrated, in this Example, is a method of specifically delivering an effector moiety into cancer cells, comprising the steps of contacting the cancer cells with an iNA which is coupled to an effector moiety, wherein the iNA specifically binds to a cell surface molecule for which the iNA has binding specificity, wherein the effector moiety is delivered into the cancer cells, and minimal (little or no) delivery in nonmalignant cells tested. Minimal detection or minimal delivery into cells other than target cells can be evidenced, for example, by at least a two-fold increase (and as much as a ten-fold or more increase, depending on the cells and parameters of activity measured) of detection or delivery in the target cells (e.g., cancer cells) contacted by a modified iNA of the invention as compared to detection or delivery in or to cells other than target cells (e.g., nonmalignant cells) contacted with a modified iNA of the invention.

EXAMPLE 6

In this Example, illustrated are: (a) modification of an iNA with an effector moiety (in addition to the illustrations in Examples 2-5 herein); (b) modification of an iNA with an effector molecule comprising a drug, in forming an iNA-drug conjugate; (c) a demonstration that the modified iNA comprising an iNA-drug conjugate can bind to and internalize into target cells comprising cancer cells; (d) a demonstration of the specificity for an iNA-drug conjugate for target cells comprising cancer cells, while showing little or no detectable activity on normal (nonmalignant) tissue cells tested; (e) a tumor-specific drug conjugate comprising an internalizing nucleic acid molecule modified with a linker and a cytotoxic drug (with the linker having a first portion to which is coupled to the iNA, and a second portion to which is coupled the cytotoxic drug); (f) a method of delivering at least one effector moiety into target cells, the method comprising contacting the target cells with an iNA modified with a linker and at least one effector moiety, wherein the effector moiety is delivered into the cytoplasm of the target cells; and (g) a method of treating, preventing, and/or ameliorating a disease or condition associated with expression on target cells of a surface molecule for which the iNA has binding specificity, the method comprising contacting a modified iNA (iNA-linker-drug conjugate) with target cells, wherein the modified iNA is administered in an amount effective to cause cytotoxicity of the target cells.

In this example of the invention, an iNA was modified to comprise a cleavable linker and a cytotoxic drug, in forming an iNA-drug conjugate that could be cleaved inside a target cell to release the cytotoxic drug, which then allows the drug to induce cytoxicity in target cells which have internalized the iNA-drug conjugate. To illustrate this aspect, an iNA of the invention (E3) was transcribed with a 3'-extention or tail (CACGAGAGGUCCUCCGGAAGC; SEQ ID NO:40) hybridizable with a nucleic acid oligonucleotide modified to contain a thiol group on the 5'-end ([ThiSS][Sp-C18]-GCT-TCCGGAGGACCTCTCGTG; SEQ ID NO:41; Sp-C18 is a commercially available PEG linker of 18 atoms used as a spacer placed between the thiol and the 5' nucleotide of the oligonucleotide). The drug used to modify the iNA comprises a *Pseudomonas* exotoxin which (i) has been modified to reduce immunogenicity, (ii) is known to have the ability to escape endosomes because it contains a certain amino acid sequence (comprising REDL (SEQ ID NO:42) or KDEL SEQ ID NO:43) which is utilized in an endosomal transport mechanism ("translocation domain"), and (iii) comprises an amino acid sequence consisting of SEQ ID NO:44. Note, and as shown by SEQ ID NO:44, that the toxin was synthesized to contain multiple lysine residues (e.g., 4) on the N-terminus of the toxin.

The N-terminal lysine residue of the toxin was then modified to include a reactive moiety for formation of a linker. In this regard, Succinimidyl-4-(N-maleimidomethyl) cyclohexane-1-carboxylate (SMCC) was used as a cross-linker. SMCC contains an amine-reactive N-hydroxysuccinimide (NHS ester) and a sulfhydryl-reactive maleimide group, wherein the NHS esters react with primary amines at pH 7-9 to form stable amide bonds; and wherein the maleimide (reactive moiety) can react with sulfhydryl groups at pH 6.5-7.5 to form thioether bonds. To modify the toxin to include the reactive moiety, the NHS ester of SMCC was reacted with lysine residues on the toxin molecules, converting them to reactive maleimides, by reacting the toxin with Sulfo-SMCC in PBS/EDTA for 1 hour at room temperature. The Sulfo-SMCC-activated toxin was desalted by gel filtration into a borate buffer, pH 8.5, containing 150 mM NaCl, and then concentrated in a filtration unit, with a size cutoff of 10 kDa, by centrifugation. The Sulfo-SMCC activated toxin was mixed with the reduced thiol-modified oligonucleotide (SEQ ID NO:41) and incubated overnight at 4° C. The oligonucleotide-toxin conjugate was then purified by anion-exchange chromatography, and then further purified by gel filtration using column chromatography. The purified oligonucleotide-toxin conjugate was then sterilized by filtration, and concentrated using a concentrating centrifugal device. The modified iNA, comprising an iNA-drug conjugate, was formed by mixing the iNA containing the tail for hybridization (SEQ ID NO:45) with the purified oligonucleotide-toxin conjugate in a 1:1 ratio, and allowing for hybridization (between the tail and oligonucleotide) at room temperature for at least 30 minutes. If desired, the iNA-drug conjugate may be further purified using any one or more techniques known in the art such as anion-exchange chromatography. In this illustration, the linker comprised the nucleic acid tail, synthesized as part of the iNA, hybridized to the oligonucleotide, which was coupled to the toxin.

The modified iNA was then evaluated for delivery of the drug to target cells, as compared to healthy or normal (nonmalignant) cells for which an iNA of the invention has shown to lack detectable binding and internalization activity (see, e.g., Table 8). Cells were seeded into 96 well plates the day, prior to exposure to the iNA-toxin conjugate, at a concentration determined for each cell line to be optimal for logarithmic growth over the course of the experiment. Serial dilutions of the iNA-drug conjugates, or toxin only counterparts, were applied to the cells in duplicate or triplicate and incubated for 72 hours at 37° C., 5% $CO_2$. After 72 hours a dye (Cell Titer Blue (Promega)) was added to each well, and then incubated for 3 hours at 37° C., 5% $CO_2$, to assess metabolic activity of the cells. Using untreated wells of cells as a control, the metabolic activity was plotted against concentration of iNA-drug conjugate, and the concentration of the iNA-drug conjugate where the metabolic activity is reduced by half ($IC_{50}$) was determined for each cell line (see Table 10).

TABLE 10

| Cells | Toxin $IC_{50}$ (nM) | E3-Toxin $IC_{50}$ (nM) |
|---|---|---|
| malignant | | |
| PC3 | >100 | 1.1 |
| LNCaP | >100 | 0.4 |
| MCF7 | >100 | 0.07 |

TABLE 10-continued

| Cells | Toxin $IC_{50}$ (nM) | E3-Toxin $IC_{50}$ (nM) |
|---|---|---|
| T47D | >100 | 0.7 |
| SKBR3 | >100 | 0.04 |
| HCC1937 | >100 | 0.06 |
| HS578T | >100 | 2.0 |
| HCC1143 | >100 | 0.02 |
| nonmalignant | | |
| PrEC human primary prostate epithelial cells | >100 | >100 |

The results in Table 10 show that an iNA-drug conjugate of the invention can deliver a functional cytotoxic drug into tumor cells with high potency (e.g., an $IC_{50}$ of 2 nM or less), including in tumors of different types, and with high specificity (e.g., with minimal or no detectable cytotoxic effect in nonmalignant cells, such as primary prostate epithelial cells).

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept of the present invention; and thus, such modifications and/or adaptations are intended to be within the meaning and scope of the appended claims.

What is claimed is:

1. A modified internalizing nucleic acid molecule, wherein the internalizing nucleic acid molecule ("iNA"): (a) comprises RNA of from about 20 nucleotides to about 70 nucleotides and having a stem-loop structure containing at least one loop portion; wherein the at least one loop portion comprises a nucleic acid sequence containing the nucleotide sequence of UUUCGG, or UUUCGGGC, or (UUUCGG)$N_m$(UUUCGG)$_n$(SEQ ID NO:22), or a combination thereof; wherein n is a number from one to four, N is a nucleotide, and m is a number from 0 to 4; (b) is capable of binding a cell surface molecule on tumor cells, wherein the cell surface molecule is other than prostate-specific membrane antigen; (c) is modified to include at least one chemical modification, wherein the at least one modification is selected from the group consisting of incorporation of a modified nucleotide into the iNA, conjugation to a linker selected from the group consisting of a linker comprised of amino acids, and a chemical linker, and conjugation to at least one effector moiety comprising one or more of a drug or detectable moiety or combination thereof; and (d) the modified INA is capable of internalizing into tumor cells.

2. A method of delivering at least one effector moiety into target cells, the method comprising: contacting the target cells with modified internalizing nucleic acid molecule according to claim 1; wherein the modified internalizing nucleic acid molecule is internalized into the target cells, thereby delivering the at least one effector moiety into the target cells.

3. The method of claim 2, wherein the modified internalizing nucleic acid molecule comprises RNA of from about 20 nucleotides to about 70 nucleotides and having a stem-loop structure, as predicted by an RNA folding algorithm; wherein the stem-loop structure comprises at least two loop portions, wherein each of the at least two loop portions of the stem-loop structure comprises a nucleic acid sequence containing the nucleotide sequence of UUUCGG.

4. A method of treating an individual having cancer or a pre-cancerous condition, the method comprises administering to the individual a therapeutically effective amount of a modified internalizing nucleic acid molecule according to claim 1, wherein the at least one effector moiety comprises a drug, and wherein the administration treats the cancer or pre-cancerous condition.

5. A method of detection comprising (a) contacting cells with a modified internalizing nucleic acid molecule according to claim 1, wherein the at least one effector moiety comprises a detectable moiety, and (b) detecting the presence or absence of the detectable moiety in the cells.

6. A method of causing cytotoxicity to cancer cells, the method comprising contacting the cancer cells with a therapeutically effective amount of a modified internalizing nucleic acid molecule according to claim 1, wherein the at least one effector moiety comprises a drug, and wherein the modified internalizing nucleic acid molecule binds to and internalizes into the cancer cells, and causes cytotoxicity to the contacted cancer cells.

7. An internalizing nucleic acid molecule ("iNA") comprising RNA of from about 20 nucleotides to about 70 nucleotides and having a stem-loop structure, as predicted by an RNA folding algorithm, wherein the stem-loop structure comprises at least two loop portions, wherein each of the at least two loop portions of the stem-loop structure comprises a nucleic acid sequence containing the nucleotides sequence of UUUCGG or UUUCGGGC, or (UUUCGG)$N_m$(UUUCGG)$_n$(SEQ ID NO:22) wherein n is a number from one to four, N is a nucleotide, and m is a number from 0 to 4.

8. The iNA of claim 7, wherein the iNA comprises a nucleic acid molecule having a nucleic acid sequence comprising SEQ ID NO:39, SEQ ID NO:25, SEQ ID NO:26, SEQ ID NO:27, or SEQ ID NO:29 and contains the nucleotide sequence of UUUCGG, or UUUCGGGC, or (UUUCGG)$N_m$(UUUCGG)$_n$(SEQ ID NO:22) wherein n is a number from one to four, N is a nucleotide, and m is a number from 0 to 4.

9. The iNA of claim 7, wherein the iNA comprises a nucleic acid molecule having at least 80% identity to the nucleic acid sequence of SEQ ID NO:39, SEQ ID NO:25, SEQ ID NO:26, SEQ ID NO:27, or SEQ ID NO:29; and contains the nucleotide sequence of UUUCGG or UUUCGGGC, or (UUUCGG)$N_m$(UUUCGG)$_n$(SEQ ID NO:22) wherein n is a number from one to four, N is a nucleotide, and m is a number from 0 to 4.

10. The iNA of claim 7 wherein the iNA contains the nucleotide sequence of (UUUCGG)$N_m$(UUUCGG)$_n$(SEQ ID NO:22); wherein n is a number from one to four, N is a nucleotide, and m is a number from 0 to 4.

11. An internalizing nucleic acid molecule ("iNA") modified to include at least one effector moiety, wherein the at least one effector moiety comprises one or more of a drug, detectable moiety, or combination thereof, wherein the iNA:
   (a) comprises RNA that binds to a cell surface molecule on tumor cells and wherein the cell surface molecule is other than prostate-specific membrane antigen;
   (b) is capable of binding to and internalizing into more than one type of tumor cell; and
   (c) comprises RNA of from about 20 nucleotides to about 70 nucleotides having a stem-loop structure, as predicted by an RNA folding algorithm, wherein the stem-loop structure comprises at least two loop portions, wherein at least one loop portion of the stem-loop structure comprises a nucleic acid sequence containing the nucleotide sequence of UUUCGG, or UUUCGGGC, or (UUUCGG)$N_m$(UUUCGG)$_n$(SEQ ID NO:22) wherein n is a number from one to four, N is a nucleotide, and m is a number from 0 to 4, and wherein the modified iNA is internalized into the target cells, in delivering the at least one effector moiety into the target cells.

12. The iNA of claim 11, wherein the iNA is modified to include at least one chemical modification, wherein the at least one modification is selected from the group consisting of incorporation of a modified nucleotide into the iNA, conjugation to a linker selected from the group consisting of a linker comprised of amino acids, and a chemical linker, and conjugation to at least one effector moiety comprising one or more of a drug or a detectable moiety or a combination thereof.

* * * * *

SEQUENCE LISTING

```
<160> NUMBER OF SEQ ID NOS: 45

<210> SEQ ID NO 1
<211> LENGTH: 5
<212> TYPE: PRT
<213> ORGANISM: Artificial
<220> FEATURE:
<223> OTHER INFORMATION: synthesized

<400> SEQUENCE: 1

Gly Pro Pro Gly Pro
1               5

<210> SEQ ID NO 2
<211> LENGTH: 5
<212> TYPE: PRT
<213> ORGANISM: Artificial
<220> FEATURE:
<223> OTHER INFORMATION: synthesized

<400> SEQUENCE: 2

Gly Glu Ala Gly Pro
1               5

<210> SEQ ID NO 3
<211> LENGTH: 5
<212> TYPE: PRT
<213> ORGANISM: Artificial
<220> FEATURE:
<223> OTHER INFORMATION: synthesized

<400> SEQUENCE: 3

Gly Glu Thr Gly Pro
1               5
```

```
<210> SEQ ID NO 4
<211> LENGTH: 5
<212> TYPE: PRT
<213> ORGANISM: Artificial
<220> FEATURE:
<223> OTHER INFORMATION: synthesized

<400> SEQUENCE: 4

Gly Glu Ser Gly Pro
1               5

<210> SEQ ID NO 5
<211> LENGTH: 5
<212> TYPE: PRT
<213> ORGANISM: Artificial
<220> FEATURE:
<223> OTHER INFORMATION: synthesized

<400> SEQUENCE: 5

Gly Asp Thr Gly Pro
1               5

<210> SEQ ID NO 6
<211> LENGTH: 5
<212> TYPE: PRT
<213> ORGANISM: Artificial
<220> FEATURE:
<223> OTHER INFORMATION: synthesized

<400> SEQUENCE: 6

Gly Asp Ser Gly Pro
1               5

<210> SEQ ID NO 7
<211> LENGTH: 4
<212> TYPE: PRT
<213> ORGANISM: Artificial
<220> FEATURE:
<223> OTHER INFORMATION: synthesized

<400> SEQUENCE: 7

Pro Pro Gly Pro
1

<210> SEQ ID NO 8
<211> LENGTH: 4
<212> TYPE: PRT
<213> ORGANISM: Artificial
<220> FEATURE:
<223> OTHER INFORMATION: synthesized

<400> SEQUENCE: 8

Gly Phe Leu Gly
1

<210> SEQ ID NO 9
<211> LENGTH: 10
<212> TYPE: PRT
<213> ORGANISM: Artificial
<220> FEATURE:
<223> OTHER INFORMATION: synthesized

<400> SEQUENCE: 9

Gly Phe Gln Gly Val Gln Phe Ala Gly Phe
1               5                   10
```

```
<210> SEQ ID NO 10
<211> LENGTH: 10
<212> TYPE: PRT
<213> ORGANISM: Artificial
<220> FEATURE:
<223> OTHER INFORMATION: synthesized

<400> SEQUENCE: 10

Gly Phe Gly Ser Val Gln Phe Ala Gly Phe
1               5                   10

<210> SEQ ID NO 11
<211> LENGTH: 4
<212> TYPE: PRT
<213> ORGANISM: Artificial
<220> FEATURE:
<223> OTHER INFORMATION: synthesized

<400> SEQUENCE: 11

Ala Leu Ala Leu
1

<210> SEQ ID NO 12
<211> LENGTH: 4
<212> TYPE: PRT
<213> ORGANISM: Artificial
<220> FEATURE:
<223> OTHER INFORMATION: synthesized

<400> SEQUENCE: 12

Arg Val Arg Arg
1

<210> SEQ ID NO 13
<211> LENGTH: 10
<212> TYPE: PRT
<213> ORGANISM: Artificial
<220> FEATURE:
<223> OTHER INFORMATION: synthesized

<400> SEQUENCE: 13

Ala Gly Asn Arg Val Arg Arg Ser Val Gly
1               5                   10

<210> SEQ ID NO 14
<211> LENGTH: 12
<212> TYPE: PRT
<213> ORGANISM: Artificial
<220> FEATURE:
<223> OTHER INFORMATION: synthesized

<400> SEQUENCE: 14

Thr Arg His Arg Gln Pro Arg Gly Trp Glu Gln Leu
1               5                   10

<210> SEQ ID NO 15
<211> LENGTH: 13
<212> TYPE: PRT
<213> ORGANISM: Artificial
<220> FEATURE:
<223> OTHER INFORMATION: synthesized

<400> SEQUENCE: 15

Ser Asn Ser Arg Lys Lys Arg Ser Thr Ser Ala Gly Pro
1               5                   10

<210> SEQ ID NO 16
```

```
<211> LENGTH: 6
<212> TYPE: DNA
<213> ORGANISM: Artificial
<220> FEATURE:
<223> OTHER INFORMATION: synthesized; double stranded

<400> SEQUENCE: 16 agagga                                                               6

<210> SEQ ID NO 17
<211> LENGTH: 28
<212> TYPE: DNA
<213> ORGANISM: Artificial
<220> FEATURE:
<223> OTHER INFORMATION: synthesized

<400> SEQUENCE: 17
ataatccacc tatcccagta ggagaaat                                      28

<210> SEQ ID NO 18
<211> LENGTH: 60
<212> TYPE: DNA
<213> ORGANISM: Artificial
<220> FEATURE:
<223> OTHER INFORMATION: synthesized

<400> SEQUENCE: 18
tttggtcctt gtcttatgtc cagaatgcta atacgactca ctatagggag gacgatgcgg   60

<210> SEQ ID NO 19
<211> LENGTH: 40
<212> TYPE: RNA
<213> ORGANISM: Artificial
<220> FEATURE:
<223> OTHER INFORMATION: synthesized

<400> SEQUENCE: 19
uacuuucggg cuuucggcaa caucagcccc ucaggacgca                         40

<210> SEQ ID NO 20
<211> LENGTH: 40
<212> TYPE: RNA
<213> ORGANISM: Artificial
<220> FEATURE:
<223> OTHER INFORMATION: synthesized

<400> SEQUENCE: 20
uccccggauu ucggauacga ucccucaucc cuugaccgca                         40

<210> SEQ ID NO 21
<211> LENGTH: 83
<212> TYPE: RNA
<213> ORGANISM: Artificial
<220> FEATURE:
<223> OTHER INFORMATION: synthesized
<220> FEATURE:
<221> NAME/KEY: misc_RNA
<222> LOCATION: (16)..(55)
<220> FEATURE:
<221> NAME/KEY: misc_feature
<222> LOCATION: (16)..(55)
<223> OTHER INFORMATION: n is a, c, g, or u

<400> SEQUENCE: 21
gggaggacga ugcggnnnnn nnnnnnnnnn nnnnnnnnnn nnnnnnnnnn nnnnnauuuc   60
uccuacuggg auagguggau uau                                           83
```

```
<210> SEQ ID NO 22
<211> LENGTH: 13
<212> TYPE: RNA
<213> ORGANISM: Artificial
<220> FEATURE:
<223> OTHER INFORMATION: synthesized
<220> FEATURE:
<221> NAME/KEY: misc_RNA
<222> LOCATION: (7)..(7)
<223> OTHER INFORMATION: N can be any of A, U, G, C ; and the number of
      N is one to 4.
<220> FEATURE:
<221> NAME/KEY: misc_feature
<222> LOCATION: (7)..(7)
<223> OTHER INFORMATION: n is a, c, g, or u

<400> SEQUENCE: 22
uuucggnuuu cgg                                                          13

<210> SEQ ID NO 23
<211> LENGTH: 21
<212> TYPE: RNA
<213> ORGANISM: Artificial
<220> FEATURE:
<223> OTHER INFORMATION: synthesized

<400> SEQUENCE: 23
cacgagaggu ccuccggaag c                                                 21

<210> SEQ ID NO 24
<211> LENGTH: 21
<212> TYPE: DNA
<213> ORGANISM: Artificial
<220> FEATURE:
<223> OTHER INFORMATION: synthesized

<400> SEQUENCE: 24
gcttccggag gacctctcgt g                                                 21

<210> SEQ ID NO 25
<211> LENGTH: 62
<212> TYPE: RNA
<213> ORGANISM: Artificial
<220> FEATURE:
<223> OTHER INFORMATION: synthesized
<220> FEATURE:
<221> NAME/KEY: stem_loop
<222> LOCATION: (1)..(62)

<400> SEQUENCE: 25
gggaggacga ugcgguacuu ucgggcuuuc ggcaacauca gccccucagg acgcaauuuc       60
uc                                                                      62

<210> SEQ ID NO 26
<211> LENGTH: 46
<212> TYPE: RNA
<213> ORGANISM: Artificial
<220> FEATURE:
<223> OTHER INFORMATION: synthesized
<220> FEATURE:
<221> NAME/KEY: stem_loop
<222> LOCATION: (1)..(46)

<400> SEQUENCE: 26
gggugcggua cuuucgggcu uucggcaaca ucagccccuc aggacg                      46

<210> SEQ ID NO 27
```

```
<211> LENGTH: 32
<212> TYPE: RNA
<213> ORGANISM: Artificial
<220> FEATURE:
<223> OTHER INFORMATION: synthesized
<220> FEATURE:
<221> NAME/KEY: stem_loop
<222> LOCATION: (1)..(32)

<400> SEQUENCE: 27
gggaggcuuu cgggcuuucg gcaacaucag cc                                    32

<210> SEQ ID NO 28
<211> LENGTH: 22
<212> TYPE: RNA
<213> ORGANISM: Artificial
<220> FEATURE:
<223> OTHER INFORMATION: synthesized
<220> FEATURE:
<221> NAME/KEY: stem_loop
<222> LOCATION: (1)..(22)

<400> SEQUENCE: 28
gggaggcugg gcuuucggca ac                                               22

<210> SEQ ID NO 29
<211> LENGTH: 46
<212> TYPE: RNA
<213> ORGANISM: Artificial
<220> FEATURE:
<223> OTHER INFORMATION: synthesized
<220> FEATURE:
<221> NAME/KEY: stem_loop
<222> LOCATION: (1)..(46)

<400> SEQUENCE: 29
gggugcgaaa cuucgggcu uucggcaaca ucagccccuc agaccg                      46

<210> SEQ ID NO 30
<211> LENGTH: 46
<212> TYPE: RNA
<213> ORGANISM: Artificial
<220> FEATURE:
<223> OTHER INFORMATION: synthesized
<220> FEATURE:
<221> NAME/KEY: stem_loop
<222> LOCATION: (1)..(46)

<400> SEQUENCE: 30
gggugcggua cuaaagggcu uucggcaaca ucagcccaaa aggacg                     46

<210> SEQ ID NO 31
<211> LENGTH: 46
<212> TYPE: RNA
<213> ORGANISM: Artificial
<220> FEATURE:
<223> OTHER INFORMATION: synthesized
<220> FEATURE:
<221> NAME/KEY: stem_loop
<222> LOCATION: (1)..(46)

<400> SEQUENCE: 31
gggugcggua cuuucgggcu aaaggcaaca ucagccccuc aggacg                     46

<210> SEQ ID NO 32
<211> LENGTH: 46
<212> TYPE: RNA
<213> ORGANISM: Artificial
<220> FEATURE:
```

<223> OTHER INFORMATION: synthesized
<220> FEATURE:
<221> NAME/KEY: stem_loop
<222> LOCATION: (1)..(46)

<400> SEQUENCE: 32
gggugcggua cuuucgggcu uucaaaaaca ucagcccuc aggacg    46

<210> SEQ ID NO 33
<211> LENGTH: 46
<212> TYPE: RNA
<213> ORGANISM: Artificial
<220> FEATURE:
<223> OTHER INFORMATION: synthesized
<220> FEATURE:
<221> NAME/KEY: stem_loop
<222> LOCATION: (1)..(46)

<400> SEQUENCE: 33
gggugcggua cuuucgggcu uucggcuuua ucagcccuc aggacg    46

<210> SEQ ID NO 34
<211> LENGTH: 46
<212> TYPE: RNA
<213> ORGANISM: Artificial
<220> FEATURE:
<223> OTHER INFORMATION: synthesized
<220> FEATURE:
<221> NAME/KEY: stem_loop
<222> LOCATION: (1)..(46)

<400> SEQUENCE: 34
gggugcggua cuuucgggcu uucggcccca ucagcccuc aggacg    46

<210> SEQ ID NO 35
<211> LENGTH: 46
<212> TYPE: RNA
<213> ORGANISM: Artificial
<220> FEATURE:
<223> OTHER INFORMATION: synthesized
<220> FEATURE:
<221> NAME/KEY: stem_loop
<222> LOCATION: (1)..(46)

<400> SEQUENCE: 35
gggugcggua cuuucgggcu uucggcaacu auagcccuc aggacg    46

<210> SEQ ID NO 36
<211> LENGTH: 46
<212> TYPE: RNA
<213> ORGANISM: Artificial
<220> FEATURE:
<223> OTHER INFORMATION: synthesized
<220> FEATURE:
<221> NAME/KEY: stem_loop
<222> LOCATION: (1)..(46)

<400> SEQUENCE: 36
gggugcggua cuuucgggcu ggcacuuucg aaagcccuc aggacg    46

<210> SEQ ID NO 37
<211> LENGTH: 70
<212> TYPE: RNA
<213> ORGANISM: Artificial
<220> FEATURE:
<223> OTHER INFORMATION: synthesized
<220> FEATURE:
<221> NAME/KEY: stem_loop
<222> LOCATION: (1)..(70)

<400> SEQUENCE: 37
aagguacucu gugcuugucg augugyauug auggcacuuu cgagucaacg aguugacagg    60
acaaguaguc                                                          70

<210> SEQ ID NO 38
<211> LENGTH: 83
<212> TYPE: RNA
<213> ORGANISM: Artificial
<220> FEATURE:
<223> OTHER INFORMATION: synthesized
<220> FEATURE:
<221> NAME/KEY: stem_loop
<222> LOCATION: (1)..(83)

<400> SEQUENCE: 38
gggaggacga ugcgguccccc ggauuucgga uacgaucccu caucccuuga ccgcaauuuc   60
uccuacuggg auagguggau uau                                           83

<210> SEQ ID NO 39
<211> LENGTH: 83
<212> TYPE: RNA
<213> ORGANISM: Artificial
<220> FEATURE:
<223> OTHER INFORMATION: synthesized
<220> FEATURE:
<221> NAME/KEY: stem_loop
<222> LOCATION: (1)..(83)

<400> SEQUENCE: 39
gggaggacga ugcgguacuu ucgggcuuuc ggcaacauca gccccucagg acgcaauuuc    60
uccuacuggg auagguggau uau                                           83

<210> SEQ ID NO 40
<211> LENGTH: 21
<212> TYPE: RNA
<213> ORGANISM: Artificial
<220> FEATURE:
<223> OTHER INFORMATION: synthesized

<400> SEQUENCE: 40
cacgagaggu ccuccggaag c                                             21

<210> SEQ ID NO 41
<211> LENGTH: 21
<212> TYPE: DNA
<213> ORGANISM: Artificial
<220> FEATURE:
<223> OTHER INFORMATION: synthesized

<400> SEQUENCE: 41
gcttccggag gacctctcgt g                                             21

<210> SEQ ID NO 42
<211> LENGTH: 4
<212> TYPE: PRT
<213> ORGANISM: Artificial
<220> FEATURE:
<223> OTHER INFORMATION: synthesized

<400> SEQUENCE: 42

Arg Glu Asp Leu
1

```
<210> SEQ ID NO 43
<211> LENGTH: 4
<212> TYPE: PRT
<213> ORGANISM: Artificial
<220> FEATURE:
<223> OTHER INFORMATION: synthesized

<400> SEQUENCE: 43

Lys Asp Glu Leu
1

<210> SEQ ID NO 44
<211> LENGTH: 245
<212> TYPE: PRT
<213> ORGANISM: Artificial
<220> FEATURE:
<223> OTHER INFORMATION: synthesized

<400> SEQUENCE: 44

Met Lys Lys Lys His His His His His Ala Ser Gly Gly Arg
1               5                   10                  15

His Arg Gln Pro Arg Gly Trp Glu Gln Leu Pro Thr Gly Ala Glu Phe
            20                  25                  30

Leu Gly Asp Gly Gly Ala Val Ser Phe Ser Thr Arg Gly Thr Gln Asn
        35                  40                  45

Trp Thr Val Glu Arg Leu Leu Gln Ala His Arg Gln Leu Glu Glu Gly
    50                  55                  60

Gly Tyr Val Phe Val Gly Tyr His Gly Thr Phe Leu Glu Ala Ala Gln
65                  70                  75                  80

Ser Ile Val Phe Gly Gly Val Arg Ala Arg Ser Gln Asp Leu Asp Ala
                85                  90                  95

Ile Trp Ala Gly Phe Tyr Ile Ala Gly Asp Pro Ala Leu Ala Tyr Gly
            100                 105                 110

Tyr Ala Gln Asp Gln Glu Pro Asp Ala Ala Gly Arg Ile Arg Asn Gly
        115                 120                 125

Ala Leu Leu Arg Val Tyr Val Pro Arg Ser Ser Leu Pro Gly Phe Tyr
    130                 135                 140

Ala Thr Ser Leu Thr Leu Ala Ala Pro Glu Ala Ala Gly Glu Val Glu
145                 150                 155                 160

Arg Leu Ile Gly His Pro Leu Pro Leu Arg Leu Asp Ala Ile Thr Gly
                165                 170                 175

Pro Glu Glu Ser Gly Gly Arg Leu Glu Thr Ile Leu Gly Trp Pro Leu
            180                 185                 190

Ala Glu Arg Thr Val Val Ile Pro Ser Ala Ile Pro Thr Asp Pro Arg
        195                 200                 205

Asn Val Gly Gly Asp Leu Asp Pro Ser Ser Ile Pro Asp Ser Glu Ala
    210                 215                 220

Ala Ile Ser Ala Leu Pro Asp Tyr Ala Ser Gln Pro Gly Lys Pro Pro
225                 230                 235                 240

Arg Glu Asp Leu Lys
                245

<210> SEQ ID NO 45
<211> LENGTH: 104
<212> TYPE: RNA
<213> ORGANISM: Artificial
<220> FEATURE:
<223> OTHER INFORMATION: synthesized
<220> FEATURE:
<221> NAME/KEY: stem_loop
```

```
<222> LOCATION: (1)..(104)

<400> SEQUENCE: 45
gggaggacga ugcgguacuu ucgggcuuuc ggcaacauca gccccucagg acgcaauuuc      60
uccuacuggg auagguggau uaucacgaga gguccuccgg aagc                     104
```